United States Patent
Keller et al.

(10) Patent No.: US 6,182,655 B1
(45) Date of Patent: Feb. 6, 2001

(54) INHALER FOR MULTIPLE DOSED ADMINISTRATION OF A PHARMACOLOGICAL DRY POWDER

(75) Inventors: Manfred Keller, Bad Krozingen (DE); Thomas Eggimann, Pratteln (CH)

(73) Assignee: Jago Research AG, Muttenz (CH)

( * ) Notice: Under 35 U.S.C. 154(b), the term of this patent shall be extended for 0 days.

(21) Appl. No.: 09/077,387

(22) PCT Filed: Dec. 5, 1996

(86) PCT No.: PCT/CH96/00430
§ 371 Date: May 28, 1998
§ 102(e) Date: May 28, 1998

(87) PCT Pub. No.: WO97/20589
PCT Pub. Date: Jun. 12, 1997

(30) Foreign Application Priority Data

Dec. 7, 1995 (CH) .................................................. 3463/95

(51) Int. Cl.[7] .................. A61M 15/00; A61M 16/00; B05D 7/14; B65D 83/06

(52) U.S. Cl. ................. 128/203.15; 128/203.12

(58) Field of Search ............... 128/203.12, 203.15; 64/38; 222/636

(56) References Cited

U.S. PATENT DOCUMENTS

| | | | |
|---|---|---|---|
| 2,670,739 | * 3/1954 | McNeill | 128/203.12 |
| 3,603,308 | 9/1971 | Spradling et al. | |
| 3,837,341 | * 9/1974 | Bell | 128/203.15 |
| 3,838,686 | * 10/1974 | Szekely | 128/203.12 |
| 4,116,195 | * 9/1978 | James | 128/203.15 |
| 4,210,140 | * 7/1980 | James et al. | 128/203.15 |
| 4,227,522 | 10/1980 | Carris | |
| 4,739,754 | * 4/1988 | Shaner | 128/203.15 |
| 4,907,583 | * 3/1990 | Wetterlin et al. | 128/203.15 |
| 4,945,929 | * 8/1990 | Egilmex | 131/273 |
| 5,033,463 | * 7/1991 | Cocozza | 128/203.21 |
| 5,113,855 | * 5/1992 | Newhouse | 128/203.12 |

(List continued on next page.)

FOREIGN PATENT DOCUMENTS

| | | |
|---|---|---|
| 3336486 | 4/1984 | (DE) . |
| 8801258 | 5/1988 | (DE) . |
| 69102928 | 11/1992 | (DE) . |
| 4211475 | 6/1993 | (DE) . |
| 4208880 | 9/1993 | (DE) . |
| 4415462 | 8/1995 | (DE) . |
| 4440563 | 5/1996 | (DE) . |
| 4440734 | 5/1996 | (DE) . |
| 19523516 | 10/1996 | (DE) . |
| 19522416 | 1/1997 | (DE) . |
| 19645411 | 5/1998 | (DE) . |
| 19647947 | 5/1998 | (DE) . |

(List continued on next page.)

Primary Examiner—John G. Weiss
Assistant Examiner—Joseph F. Weiss, Jr.
(74) Attorney, Agent, or Firm—Selitto & Associates

(57) ABSTRACT

An inhaler for multiple dosed administration of a pharmacological dry powder consists externally of a housing (100, 150) and of a protective cap (950) which can be removed from a special mouthpiece (900) fitted on the housing. Arranged on the inside there are a slide rail (200), a dosing slide (300), a shutter (400), a carriage (500), a funnel arrangement (600), a counter device (700), a valve shield (800) and a valve guide (850). Removal of the protective cap (950) initiates the dosing, with a dose received in the dosing cavity (302) being transported to the mouth-piece (900) by means of the dosing slide (300). Only upon application of a defined minimum intensity of inhalation is the shutter (400) moved by the suctioned valve shield (800), as a result of which the dose is released for inhalation. Completed with an electronic module and a controllable nozzle, all inhalation-relevant data can be recorded and the flow conditions regulated.

40 Claims, 28 Drawing Sheets

U.S. PATENT DOCUMENTS

Figure 1E:
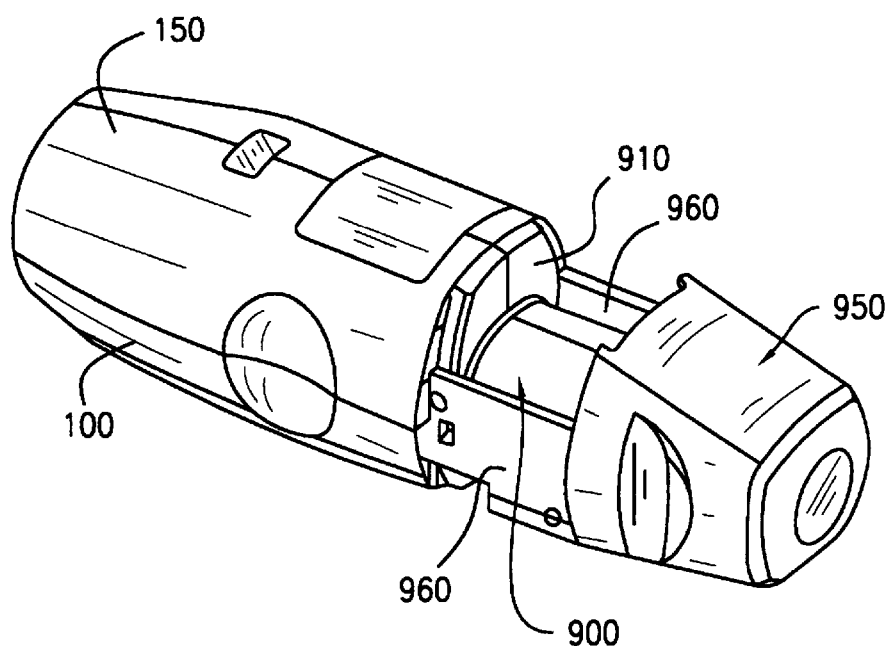

| | | | |
|---|---|---|---|
| 5,201,308 | * | 4/1993 | Newhouse ..................... 128/203.15 |
| 5,239,992 | | 8/1993 | Bougamont et al. . |
| 5,320,094 | | 6/1994 | Laube et al. . |
| 5,320,714 | * | 6/1994 | Brendel ..................... 128/203.15 |
| 5,331,953 | * | 7/1994 | Andersson et al. ............. 128/200.14 |
| 5,388,574 | * | 2/1995 | Ingebrethsen ................... 128/203.17 |
| 5,429,122 | * | 7/1995 | Zanen et al. .................... 128/203.15 |
| 5,431,154 | | 7/1995 | Seigel et al. . |
| 5,483,954 | * | 1/1996 | Mecikalski ..................... 128/203.15 |
| 5,490,502 | | 2/1996 | Rapoport et al. . |
| 5,507,281 | * | 4/1996 | Kuhnel et al. ................... 128/203.15 |
| 5,549,101 | * | 8/1996 | Trofast et al. ................... 128/203.15 |
| 5,582,162 | * | 12/1996 | Petersson ....................... 128/203.15 |
| 5,622,166 | | 4/1997 | Eisele et al. . |
| 5,645,050 | * | 7/1997 | Zierenberg et al. ............. 128/203.15 |
| 5,676,130 | * | 10/1997 | Gupte et al. .................... 128/203.19 |
| 5,678,538 | * | 10/1997 | Drought ......................... 128/203.15 |
| 5,685,294 | * | 11/1997 | Gupte et al. .................... 128/203.15 |
| 5,687,710 | * | 11/1997 | Ambrosio et al. ............. 128/203.15 |
| 5,724,959 | * | 3/1998 | McAughey et al. ............ 128/203.15 |
| 5,740,792 | * | 4/1998 | Ashley et al. .................. 128/203.15 |
| 5,829,429 | | 11/1998 | Hughes . |
| 5,829,434 | * | 11/1998 | Ambrosio et al. ............. 128/203.15 |
| 5,975,076 | * | 11/1999 | Yianneskis et al. ............ 128/203.15 |
| 5,996,577 | * | 12/1999 | Ohki et al. ...................... 128/203.15 |

FOREIGN PATENT DOCUMENTS

| | | | |
|---|---|---|---|
| 0237507 | | 9/1987 | (EP) . |
| 0387222 | | 9/1990 | (EP) . |
| 0404454 | | 12/1990 | (EP) . |
| 0404459 | | 3/1991 | (EP) . |
| 0547429 | | 6/1993 | (EP) . |
| 0558879 | | 8/1993 | (EP) . |
| 0407028 | | 9/1994 | (EP) . |
| 2701653 | | 2/1993 | (FR) . |
| 2262452 | | 6/1993 | (GB) . |
| 9303782 | | 3/1993 | (WO) . |
| 93/09832 | * | 5/1993 | (WO) .............................. 128/203.15 |
| 9405359 | | 3/1994 | (WO) . |
| 9414492 | | 7/1994 | (WO) . |
| 9416756 | | 8/1994 | (WO) . |
| 9725086 | | 7/1997 | (WO) . |
| 9730743 | | 8/1997 | (WO) . |
| 9826827 | | 6/1998 | (WO) . |
| 9830263 | | 7/1998 | (WO) . |
| 9841256 | | 9/1998 | (WO) . |
| 9915217 | | 4/1999 | (WO) . |

* cited by examiner

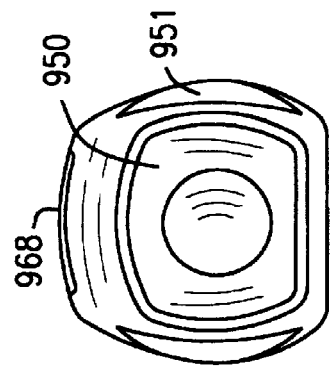
FIG. 1C
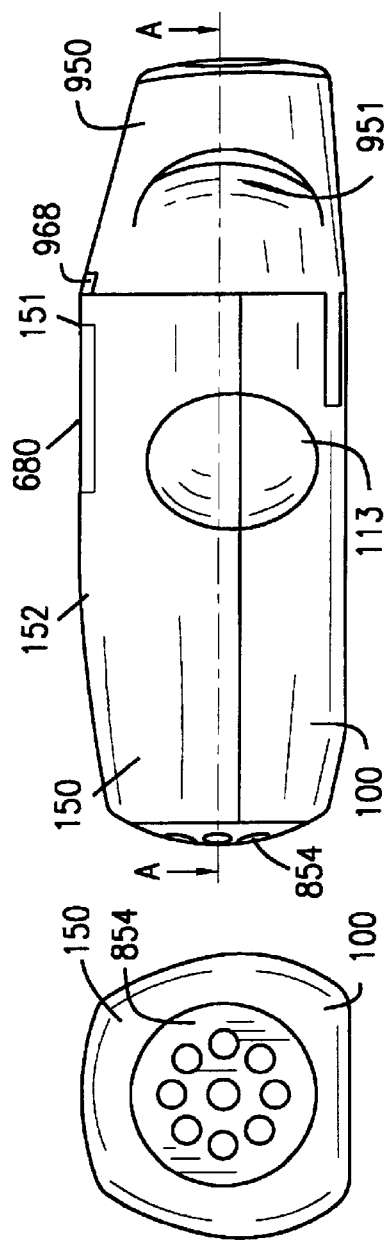
FIG. 1A
FIG. 1B
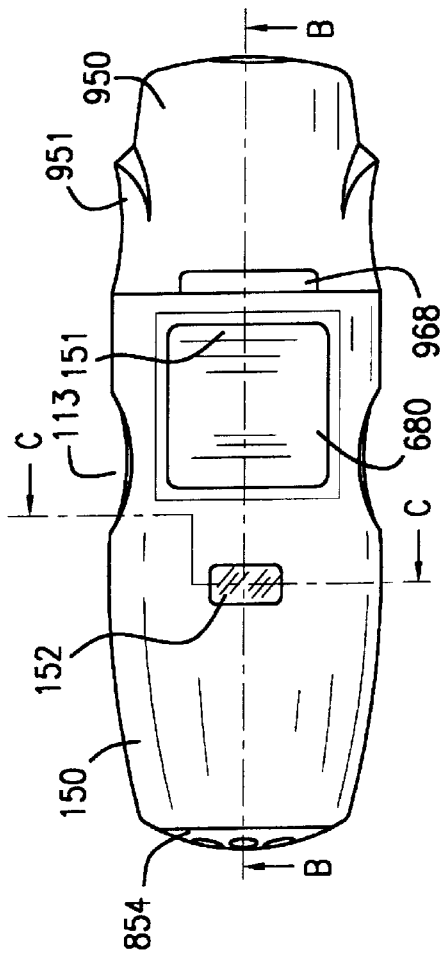
FIG. 1D

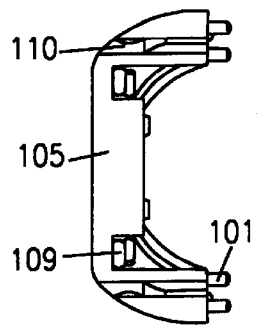
FIG. 3C
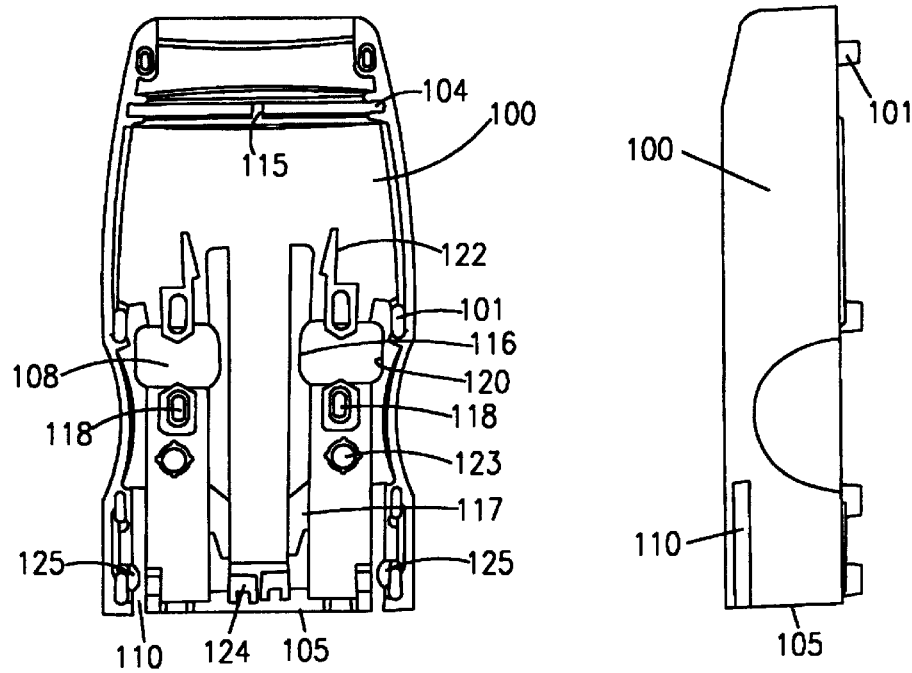
FIG. 3B
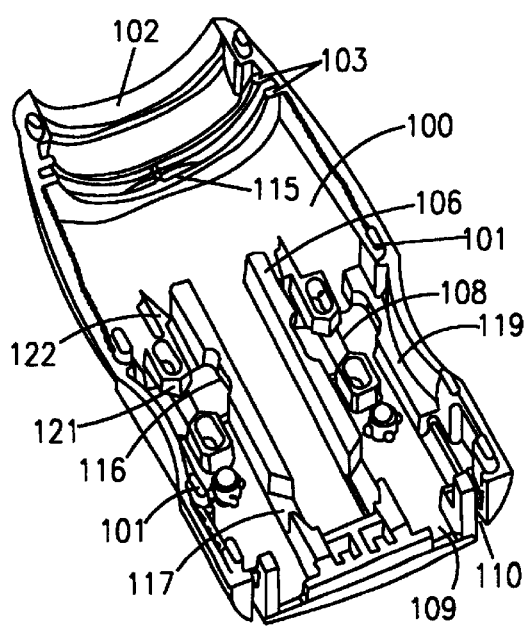
FIG. 3D
FIG. 3A

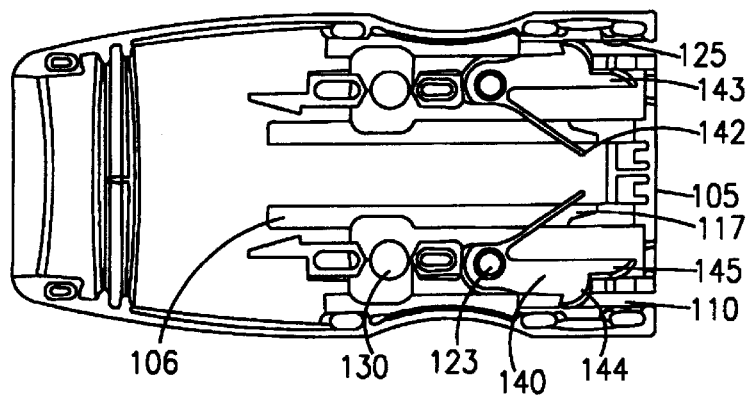
FIG. 3F
FIG. 3E
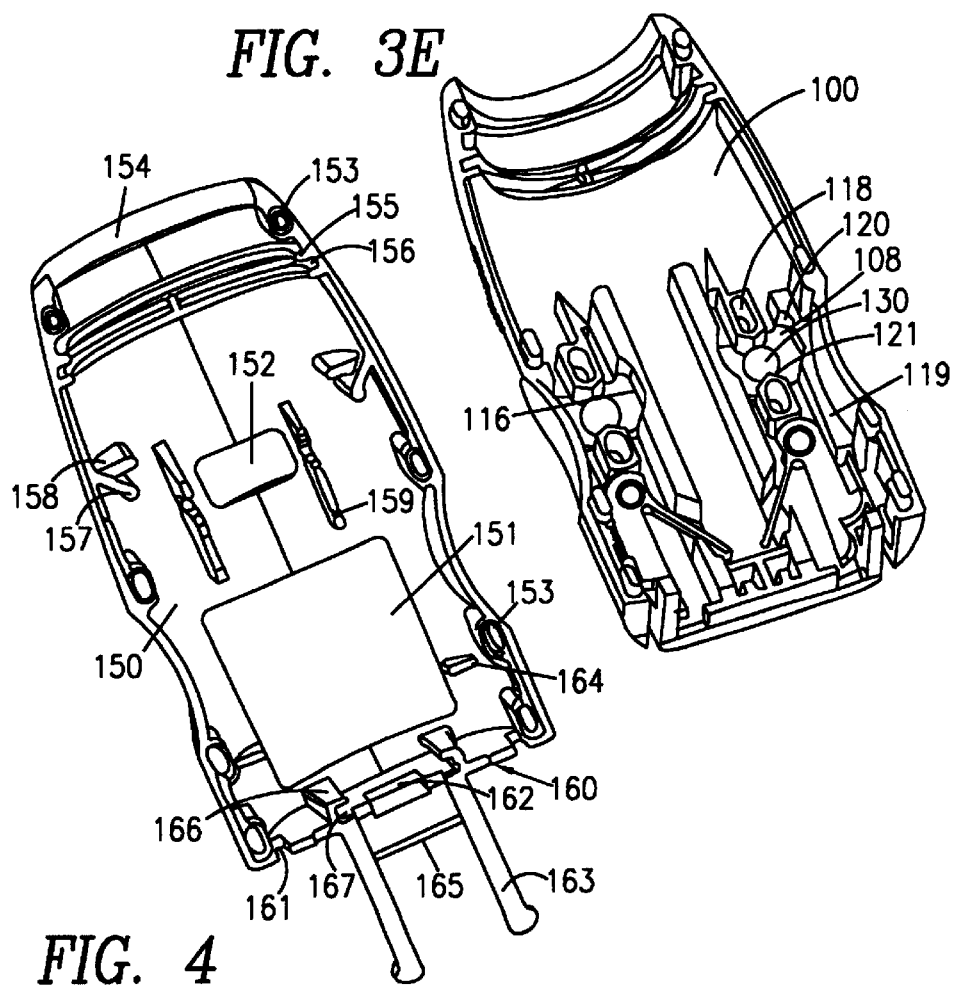
FIG. 4

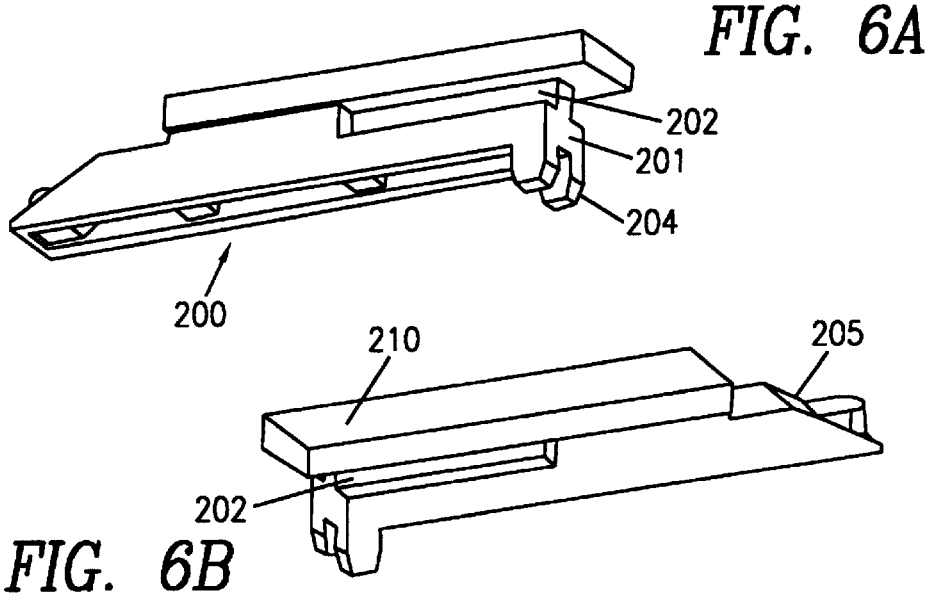
FIG. 6A
FIG. 6B
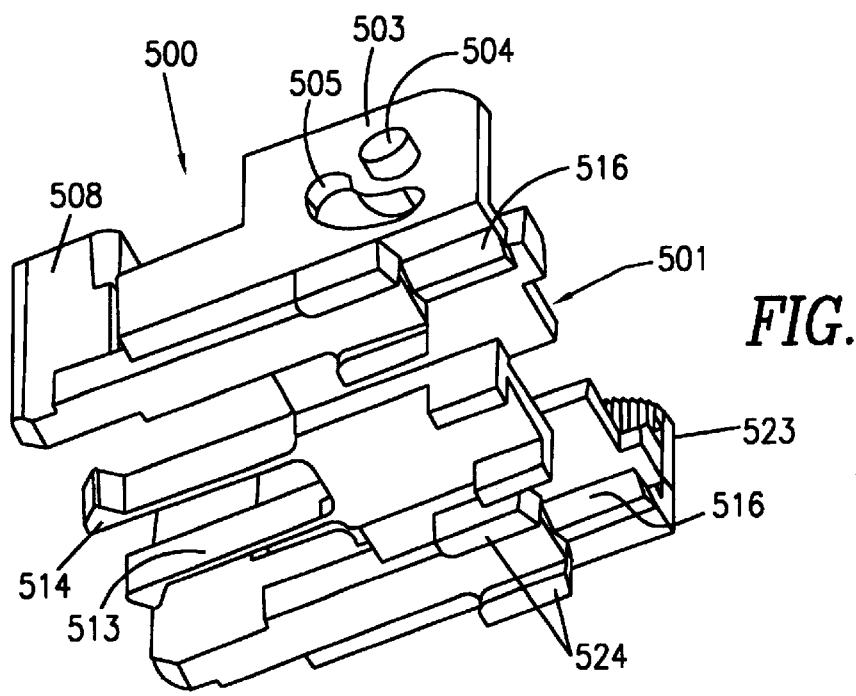
FIG. 7A

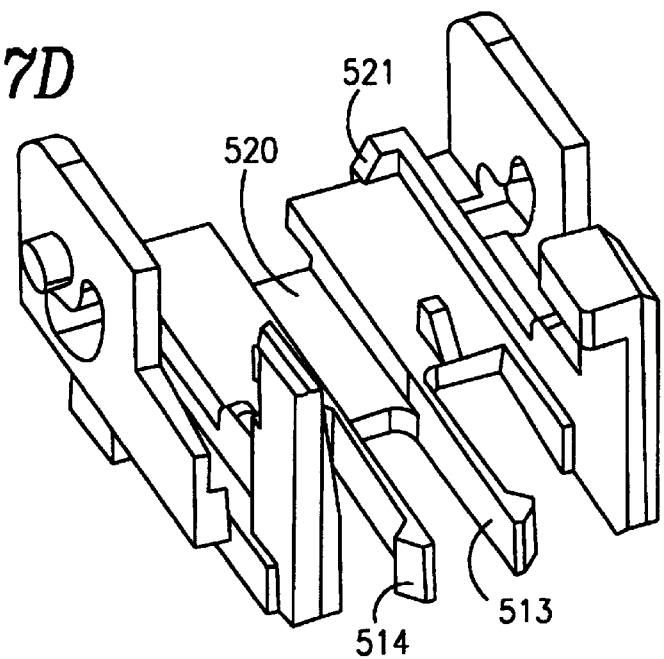
FIG. 7D
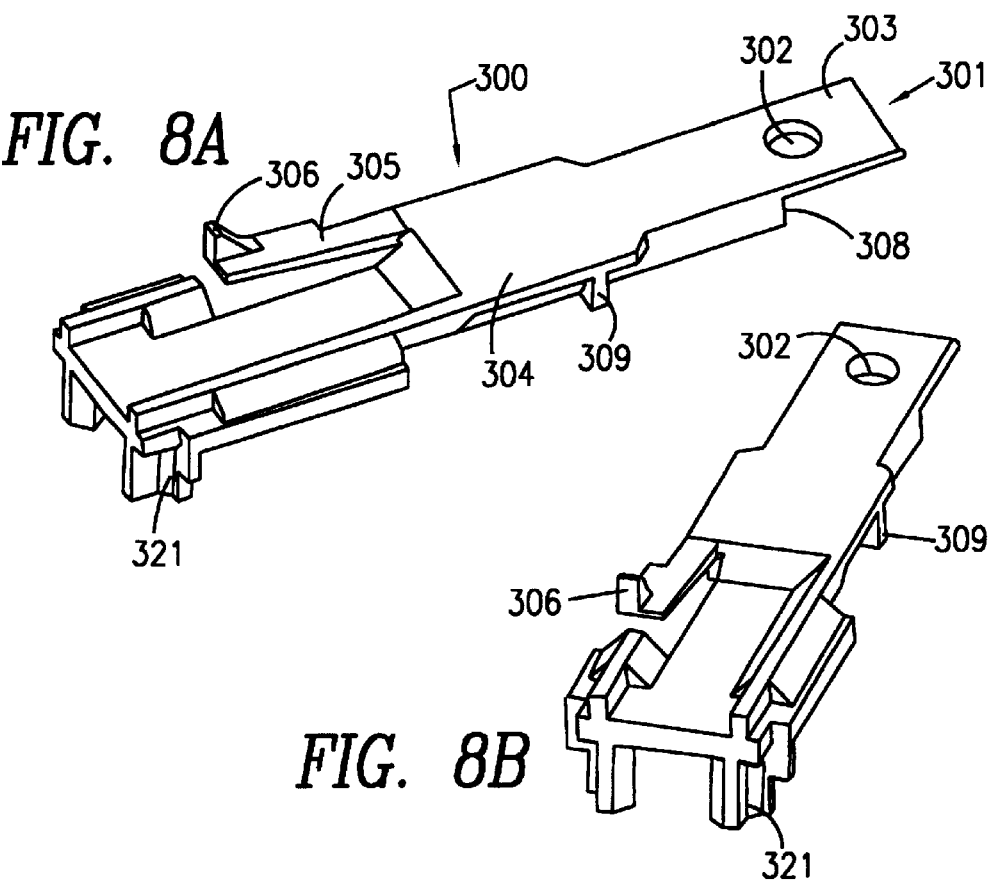
FIG. 8A
FIG. 8B

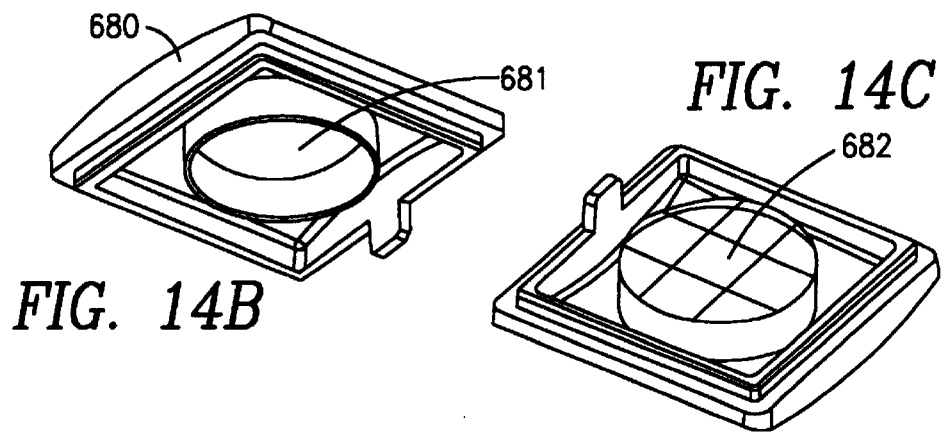
FIG. 14B  FIG. 14C
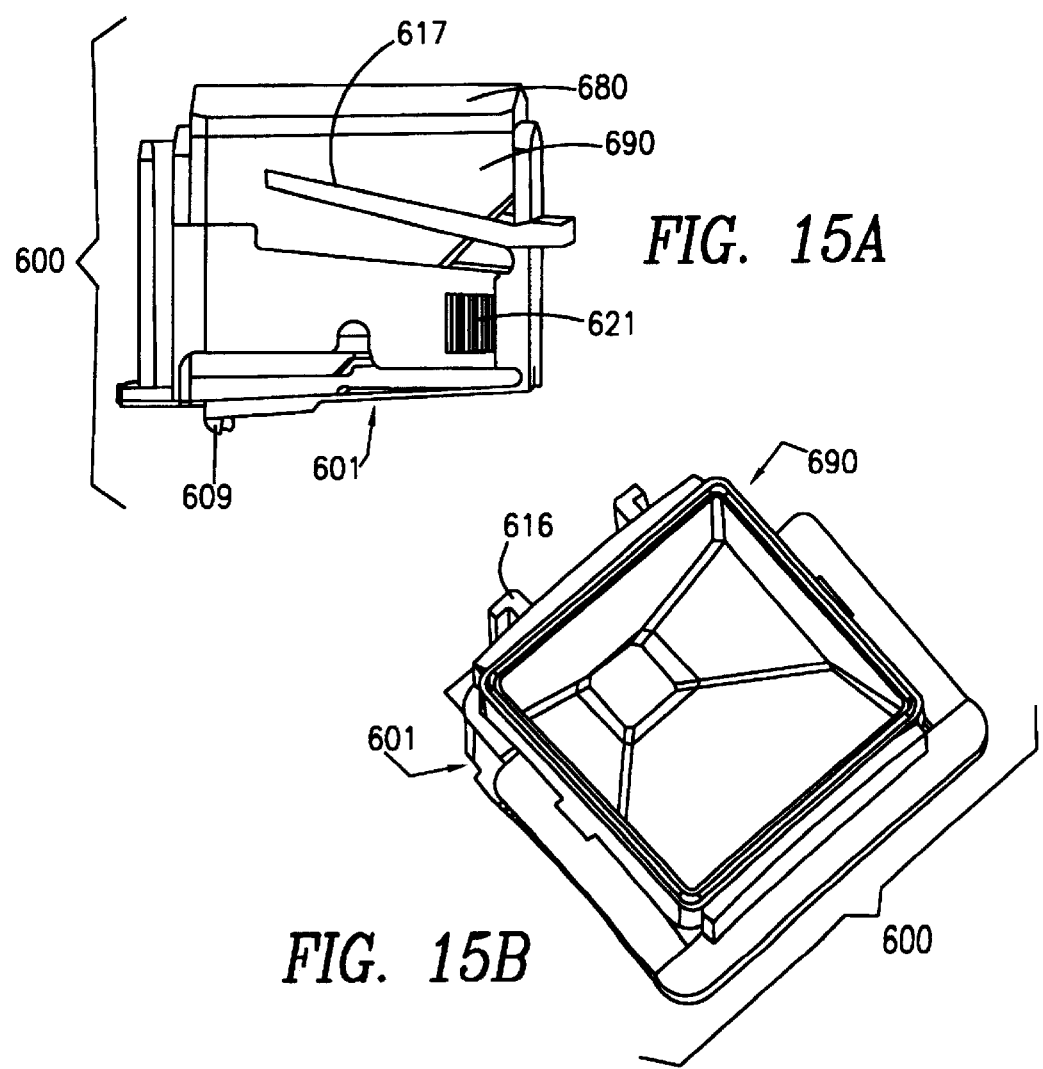
FIG. 15A
FIG. 15B

INHALER FOR MULTIPLE DOSED ADMINISTRATION OF A PHARMACOLOGICAL DRY POWDER

AREA OF APPLICATION OF THE INVENTION

The invention relates to a dry powder inhaler with dosed administration of a medical preparation upon inhalation by the patient. The dry powder—in loose form or pre-dosed units for dispensing—is contained in a medicament reservoir. The invention concerns the generic type of inhalers in which, upon activation, a defined dose is first of all introduced from the internal medicament reservoir into the inhalation channel by means of a portioning mechanism, and from there the patient draws this defined dose into his airways via a mouthpiece, in a flow of air generated by aspiration.

Inhalation is a proven method of depositing medicinal agents in the lungs or delivering them to the blood. Thus, in addition to the devices for atomizing or nebulizing of liquids, for example by means of air, compressors, ultrasound, liquefied propellant gases (fluorohydrocarbons, fluorochlorinated hydrocarbons), inhalers for pulverulent preparation with dosed portioning were also developed for the purpose of inhalation.

A defining feature of inhalers is that the active substance particles of the medicament are deposited, by inhalation, in a defined dose and particle size (about 1–6 $\mu$m) either in the central or peripheral lung compartments (topical treatment) or as very small particles by means of absorption in the alveolar region into the blood stream of the patient (systemic treatment).

However, micronized particles with the diameter in question here have extremely poor flow characteristics. This problem is solved by a number of conventional methods. Thus, powder mixtures are produced with a carrier which generally has a greater particle diameter than the active substance, with the active substance particles depositing themselves on the carrier surface. On the other hand, in the manufacture of soft pellets, a large number of active substance particles are massed together to form respectively larger particles, the pellets. Under the effect of force, the pellets split up again into the individual, smaller active substance particles. During inhalation it should be possible with the inhaler to detach the active substance particles from the carrier or to break the pellets up again into small particles. Simple swallowing of the medicament is completely undesirable. For this reason, special functional demands are imposed on inhalers in principle.

PRIOR ART

EP-A-0 404 454 and EP-A-0 558 879 disclose inhalers for single use. Such designs are appropriate only for special applications, since on the one hand the patient has no control over the correct use, i.e. the optimum inhalation, and on the other hand a new inhaler has to be used for each inhalation, which is costly, inconvenient and not environmentally friendly.

Thus, inhalers with a dry powder as medicament were developed also for multiple use. WO 93/03782 discloses an inhaler with a medicament reservoir and a dosing mechanism, by means of which the medicament is conveyed in doses from the storage container into the inhalation channel and can be sucked from there with the flow of air generated by the patient. This inhaler does not yet satisfy all the requirements. The exact and prescribed use can still not necessarily be sufficiently guaranteed. The dosing accuracy has to be increased; humidity too easily penetrates into the inhaler, the deagglomeration and atomization have to be improved, and keeping the inhaler clean is complicated.

U.S. Pat. No. 5,239,992 discloses a further inhaler in which a dosing cavity is present in a longitudinally displaceable piston rod and this dosing cavity, first positioned under the medicament reservoir, receives a dose of medicament. The patient has to inhale counter to the force of a spring, so that the piston rod moves and the ready-to-use dose can be sucked by the patient through suction openings in the guide channel of the piston rod. In principle, this inhaler too exhibits the abovementioned inadequacies.

WO 94/05359 describes an inhaler for multiple dosed administration of a pharmacological dry powder which is contained within a medicament reservoir provided inside the housing. On the inhaler a mouthpiece is joined which is closed outside inhalations by a folding down protective cap. The inhaler further has inside a horizontally movable carriage with a dosing depression. If the protective cap is closed the dosing depression is positioned underneath the funnel-shaped outlet of the medicament reservoir, so that dry powder by its gravity should flow into the dosing depression until it is full if the inhaler is in a vertical position. One filling of the depression represents one dose.

After a preceding inhalation a spring arranged above a bellows is tensed by closing the protective cap. The bellows is placed on the medicament reservoir, an air permeable membrane is provided as a separating wall. During opening the protective cap, the locking of the tensed spring is released, so an air pressure pulse acts upon the medicament reservoir. This air pressure pulse ought to guarantee that in each case the dosing depression is properly filled with dry powder. The carriage is moved by further opening of the protective cap, so the dosing depression is positioned within a suction channel. With the inhalation the medicament dose is sucked out from the dosing depression through the mouthpiece. The mouthpiece has at one side a flange for joining to the housing of the inhaler and has at the other side a suction pipe outwardly trumped-like opening. A flow channel flows tangentially into the flange which channel is connected with the suction channel, where the medicament dose is available in readiness for inhalation. At the flange, tangentially arranged air openings are provided for the purpose of turbulence of the medicament containing air stream sucked into the mouthpiece.

The spring above the bellows again tenses by closing the protection cap and the carriage goes back into its starting position, so the dosing depression is again positioned underneath the funnel-like outlet of the medicament reservoir and the next inhalation cycle can start.

The previously described inhaler and its pertinent mouthpiece shows the following essential disadvantages:
  Independent of the intensity of the inhalation, the medicament from the dosing depression can be sucked out too low such that the medicament particles only insufficiently arrive at their intended position within the patient's respiratory ducts and/or actually only a part of the dose available is sucked out. Thus the patient has no control as to whether the inhalation has been actually done or correctly completed.
  After opening the protective cap and during inhalation, the inhaler has to be positioned vertically, otherwise the dry powder can flow back from the dosing depression into the medicament reservoir or come into the suction channel situated above the dosing depression and deposit there as a loss. A construction feature is missing which obligates or requires the patient to apply the inhaler in the right functional position, i.e., not in an angled or oblique position in which the medicament does not flow or flows insufficiently into the channel inside the inhaler from which the patient inhales the powder.

At lease a part of the dry powder of the unused dose can come into the suction channel if the inhalation is incompletely finished or not done at all and the inhaler is not held strictly vertically. By the next inhalation cycle it is metered again, and therefore inaccuracies of the dosage can emerge. Based on the construction, double dosages or dosages under the limit can happen.

The extending bellows sucks in a larger amount of external air with each closing of the protective cap, thereby permitting moisture to enter the medicament reservoir. This is disadvantageous for the flowability and the accuracy of metering of the dry powder as known from the literature and the practice.

A further construction feature is missing which guarantees that the last 5 to 10 nominal doses in the declared measure (weight and volume) can be delivered in order to solve the tail-off-problem known of inhalers with a multi dosage reservoir.

The mouthpiece has at its flange a tangentially discharging channel and openings for acceleration and turbulence of the airstream generated by the patient. This corresponds with the cycle principle as used for a long time for the dry powder inhalers available on the market (e.g. SPINHALER®, CYCLONHALER®).

The unit for creating turbulence and the mouthpiece can be cleaned and dried internally relatively poorly which under certain circumstances can cause microbiological problems.

OBJECT OF THE INVENTION

Thus, in summary, it may be stated that none of the inhalers known to date can be regarded as optimal. The present invention is therefore based on the problem of producing an inhaler whose functional characteristics are extensively improved. The design construction is intended to conclusively guarantee the prescribed inhalation position and inhalation intensity. In the inhaler there must be a suitable registration and function covering a properly completed inhalation, an omitted inhalation, or an incomplete inhalation; in any event, a multiple dosage is to be prevented. It is necessary to improve the dosing accuracy upon preparation of the individual doses from the medicament reservoir, and the deagglomeration and atomization of the medicament during inhalation. The protection against humidity is to be made more effective and the cleaning of the inhaler should be made easier. It must be ensured that a mouthpiece which has been removed for cleaning is fitted in place again by the patient. The mouthpiece ought to be used as well as in connection with the inhaler to be created as with other inhalers of the present type. Finally, it must be possible for the inhaler to be manufactured efficiently as a mass-produced article and at the same time satisfy all the regulations laid down in drugs legislation.

SUMMARY OF THE INVENTION

The inhaler is used for the multiple dosed administration of a pharmacological dry powder; it consists externally of a housing and of a protective cap which can be removed from a special mouthpiece fitted on the housing. Arranged on the inside there are a slide rail, a dosing slide, a shutter, a carriage, a funnel arrangement, a counter device, a valve shield and a valve guide. Removal of the protective cap initiates the dosing, with the dose received in the dosing cavity being transported to the mouthpiece by means of the dosing slide. Only upon application of a defined minimum intensity of inhalation is the shutter moved by the suctioned valve plate, as a result of which the dose is released for inhalation. Only after a properly completed inhalation can the dosing slide be returned with its dosing cavity under the funnel outlet for the purpose of preparing for renewed filling.

In the inside of the inhaler there are blocking means which come into action as soon as the inhaler, upon removal of the protective cap, is situated in a horizontal and/or axial inclined position going beyond a defined extent. The correct dosing and use position of the inhaler are guaranteed in this way. For the patient's safety, optional blocking means can be fitted which prevent any possibility of the protective cap of the inhaler being closed when the mouthpiece is missing. This ensures that after the mouthpiece has been removed, it is not possible to omit replacing it.

In the mouthpiece, which can be detached from the housing of the rest of the inhaler, there is a labyrinthine atomizing path for powder deagglomeration, in which path there is at least one barrier. For the purpose of reducing the powder flow rate and depositing relatively coarse particles ineffective for inhalation, the atomizing path comprises, upstream of the channel outlet, a channel section which is of increased volume and which deflects the powder aerosol flowing through. The multi-component mouthpiece can preferably be arranged on the inhaler housing by means of a plug connection and can be opened out after detachment from the housing, the mouthpiece parts being connected to one another via an integral film hinge. The mouthpiece according to the invention is preferably intended for use with the inhaler according to the invention, but it is also suitable for use in connection with other inhalers of the same type.

In the inhaler there are means which contribute to the regular flow of the pharmacological dry powder when the protective cap is removed. The generated vibrations preferably only exert an effect while the dosing cavity is located under the funnel outlet. These means are advantageously complementary grate sections which are located on components moved relative to one another.

The inhaler can be supplemented with an electronic module and a controllable nozzle so that all data relevant to inhalation can be recorded and the flow conditions regulated. Completion of a correct inhalation, or an incomplete inhalation, can be indicated by an acoustic and/or optical signal.

BRIEF DESCRIPTION OF THE ATTACHED DRAWINGS

Figure 1F:
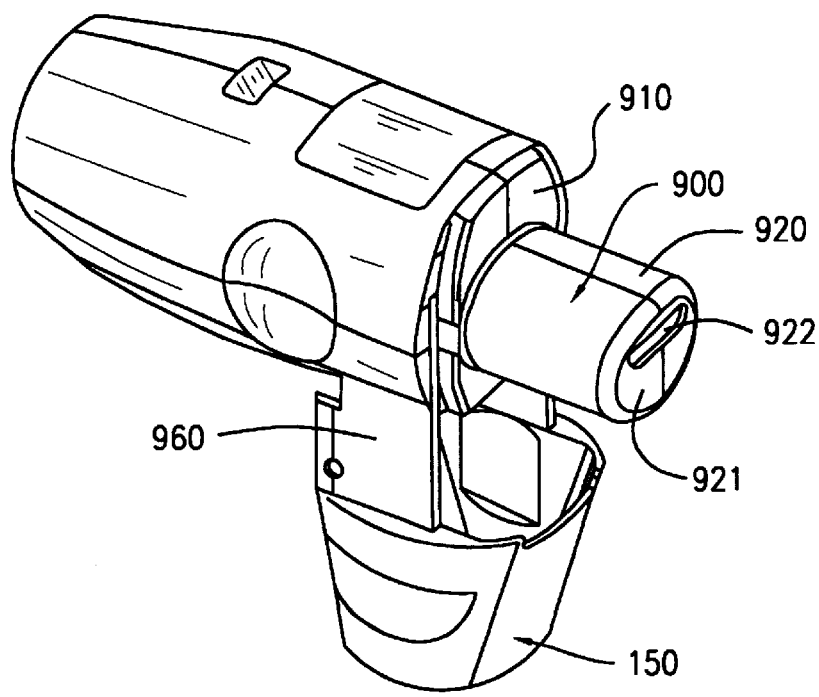
Figure 2B:
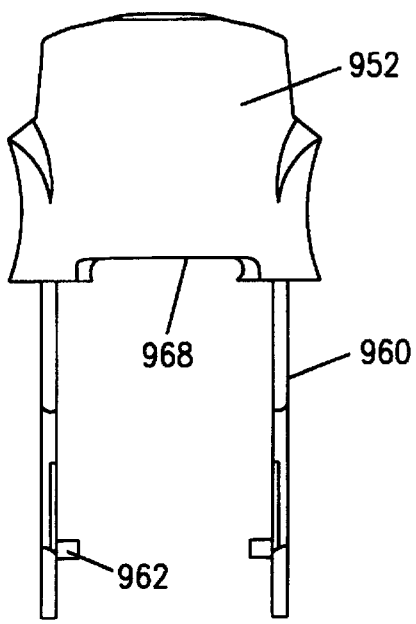
Figure 2C:
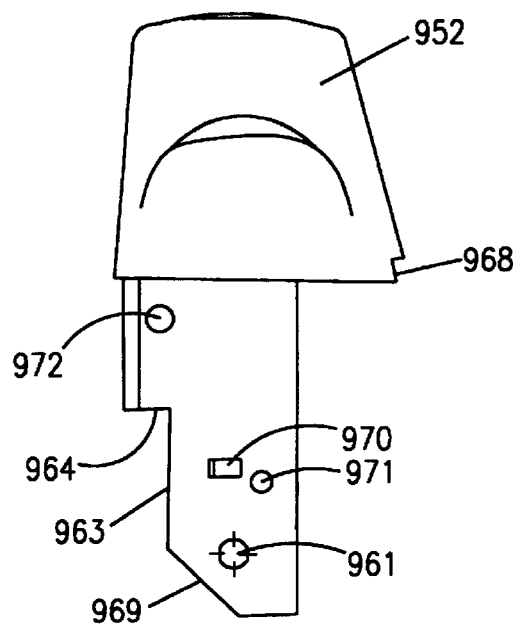
Figure 2D:
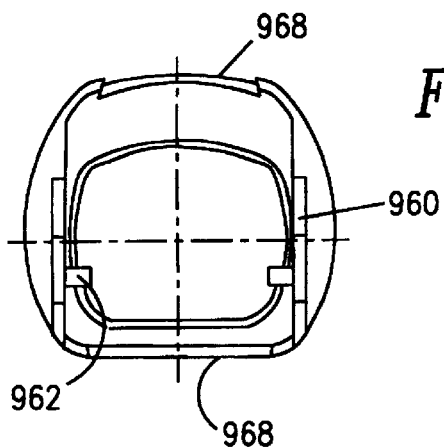
Figure 2A:
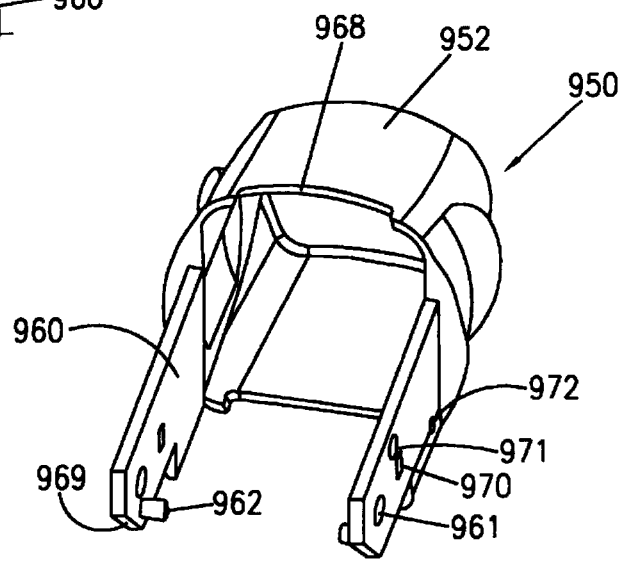
Figure 5A:
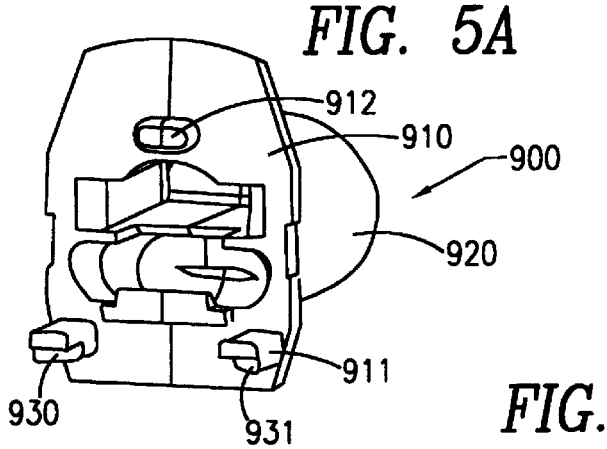
Figure 5C:
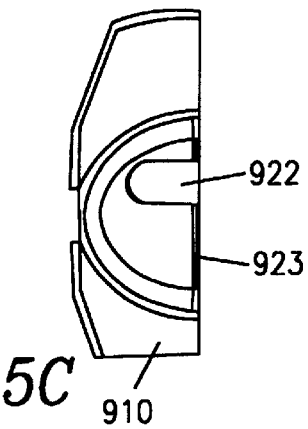
Figure 5B:
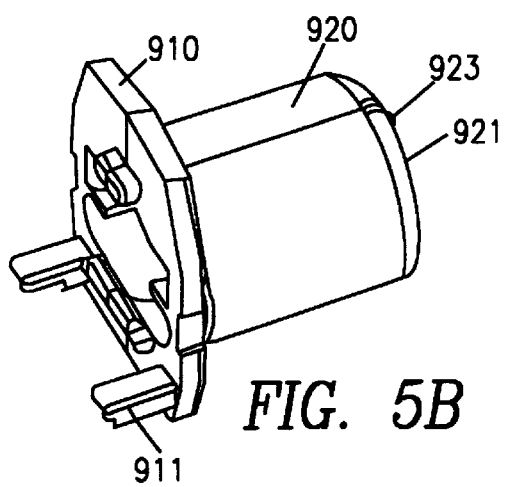
Figure 5D:
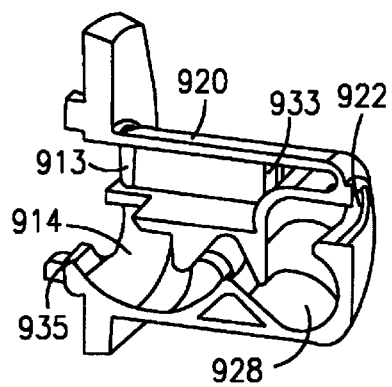
Figure 5E:
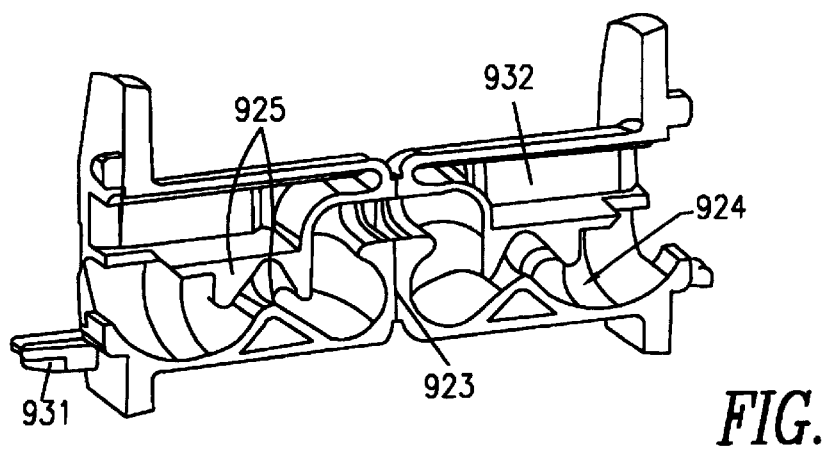
Figure 7B:
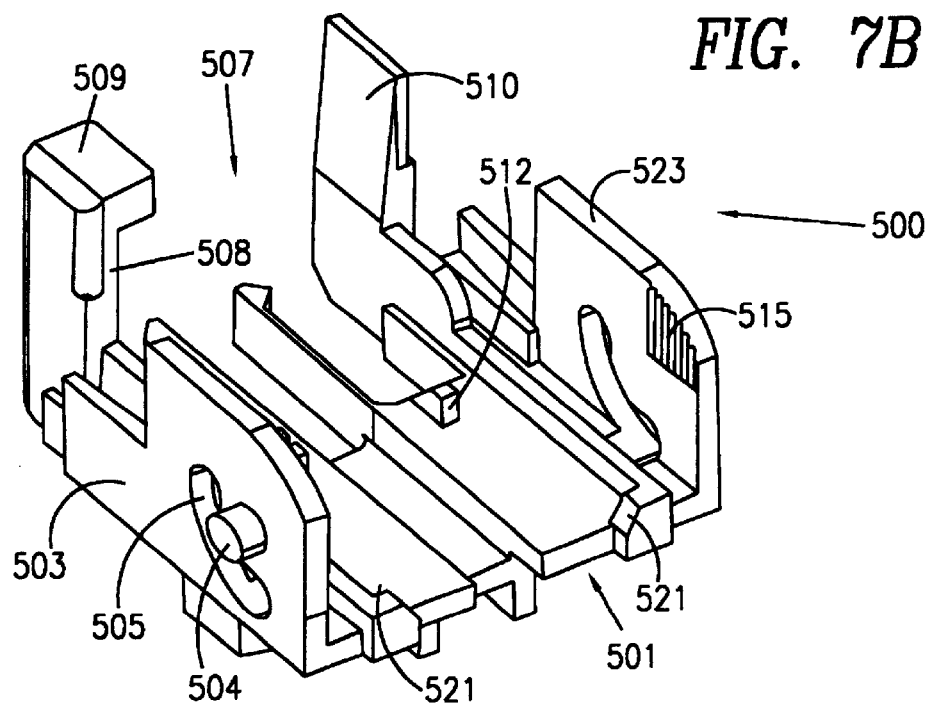
Figure 7C:
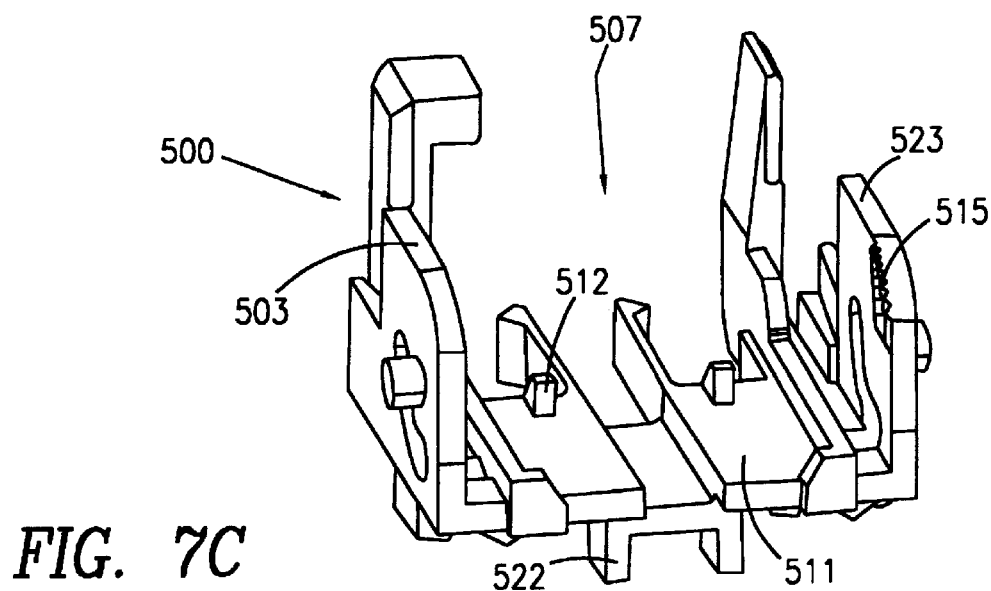
Figure 8C:
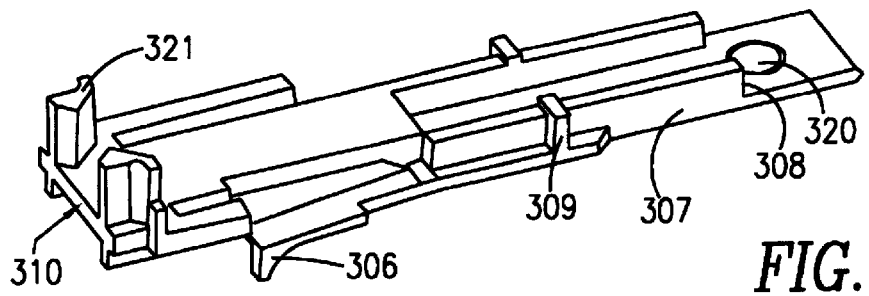
Figure 9A:
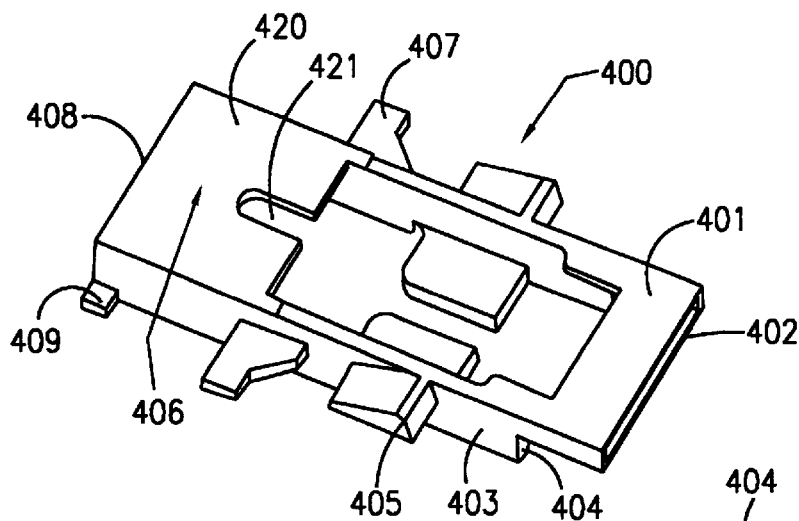
Figure 9B:
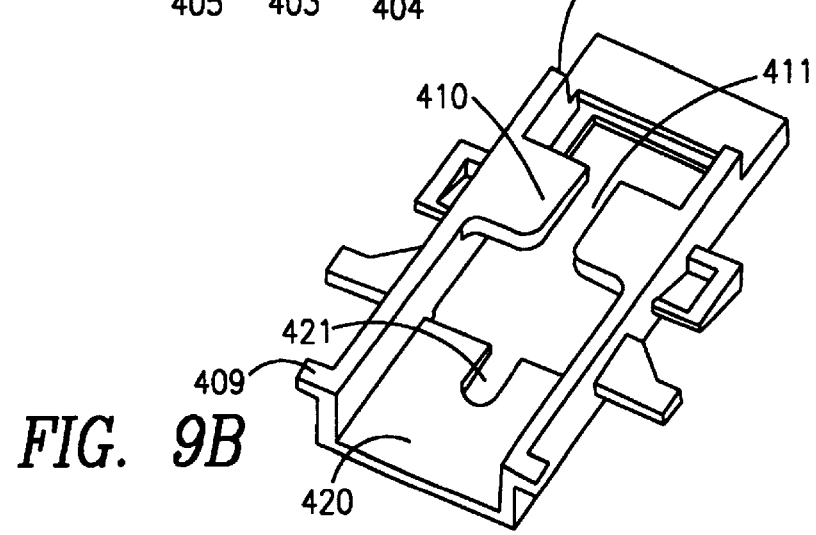
Figure 10A:
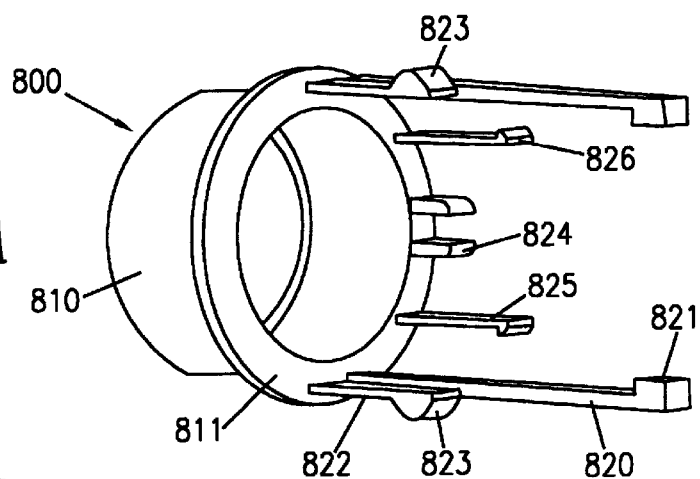
Figure 10B:
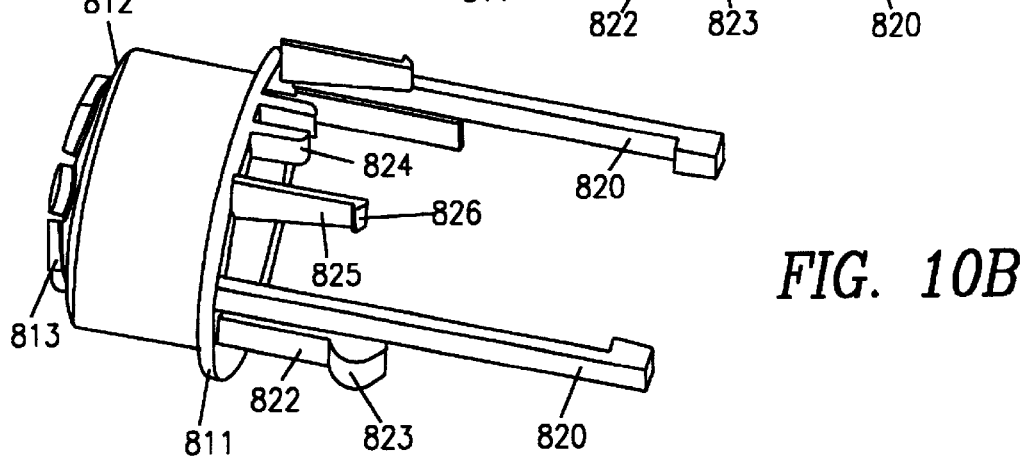
Figures 11A, 11B:
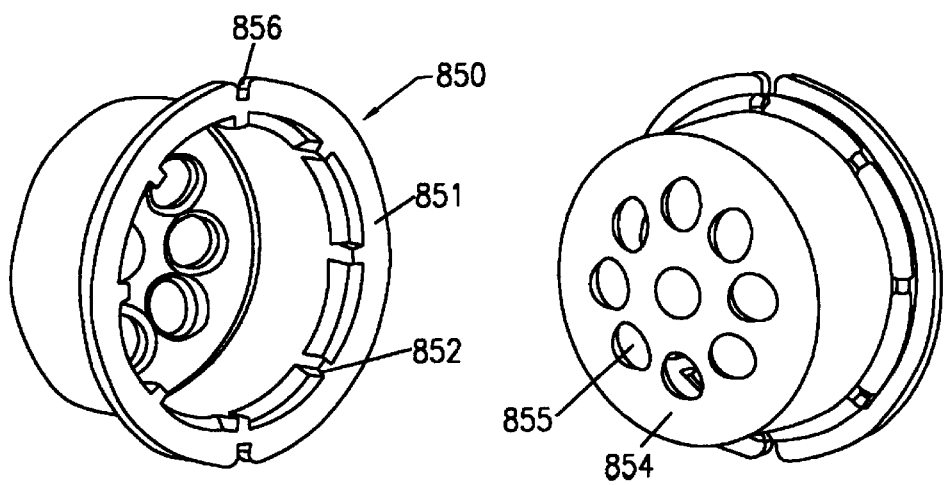
Figures 12A, 12B:
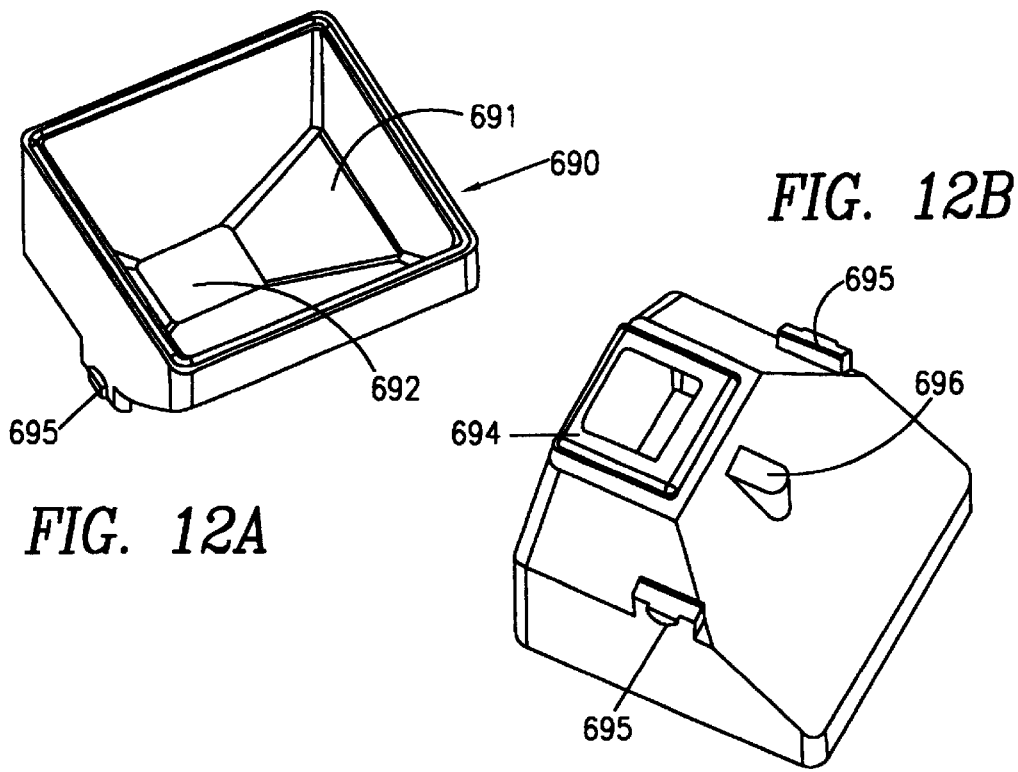
Figure 13A:
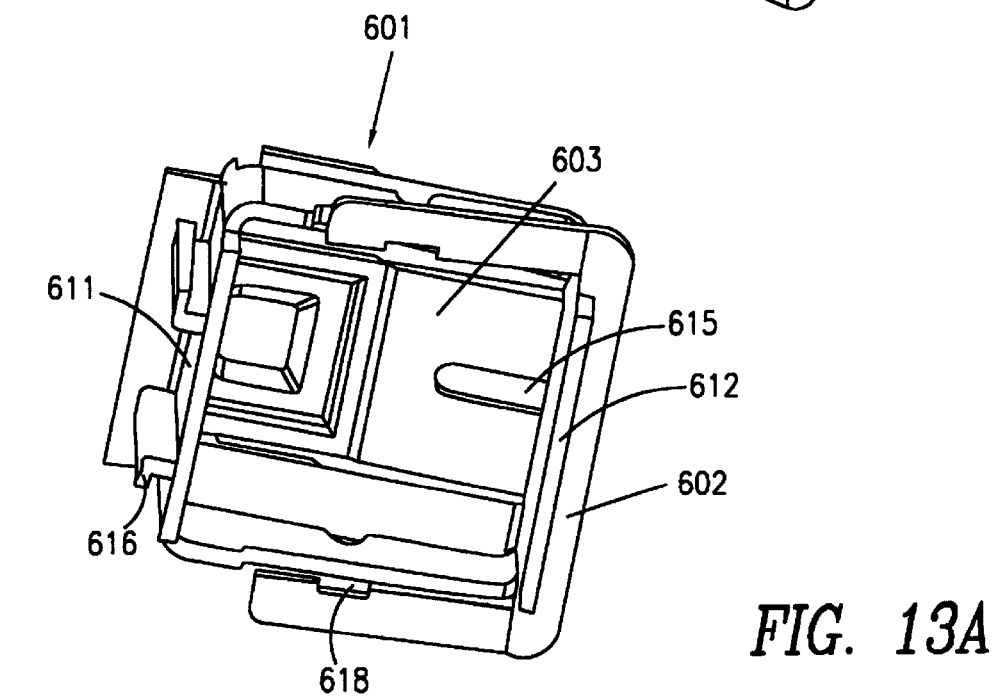
Figure 13B:
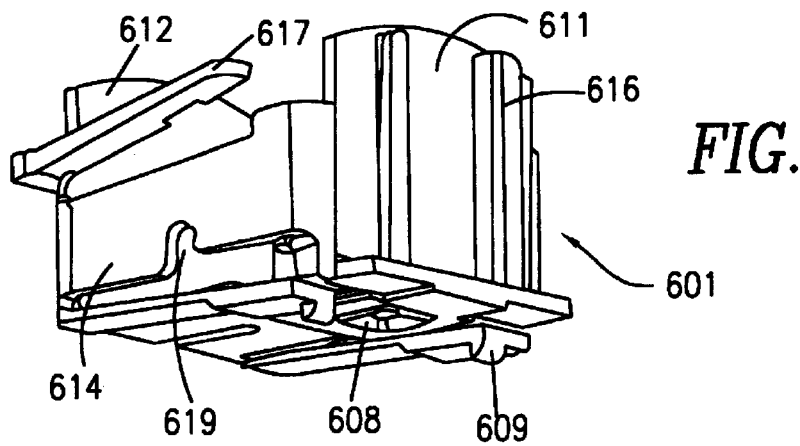
Figure 13C:
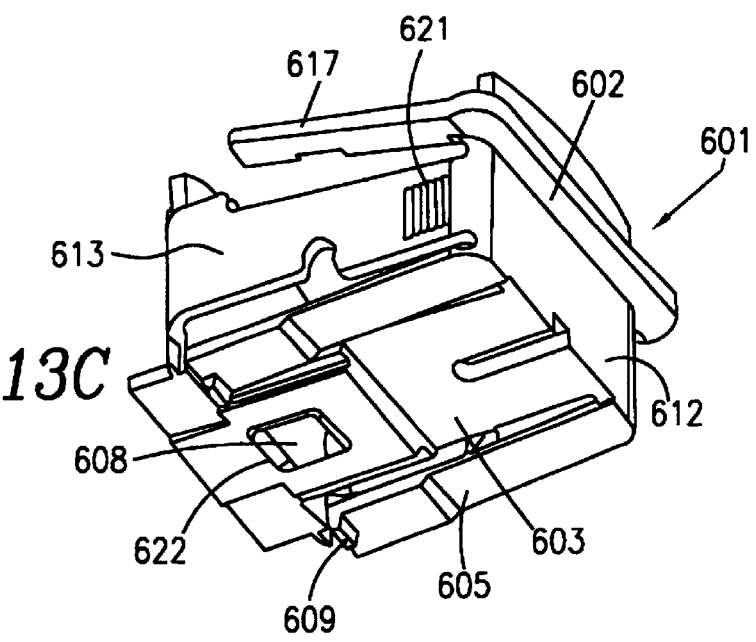
Figure 14A:
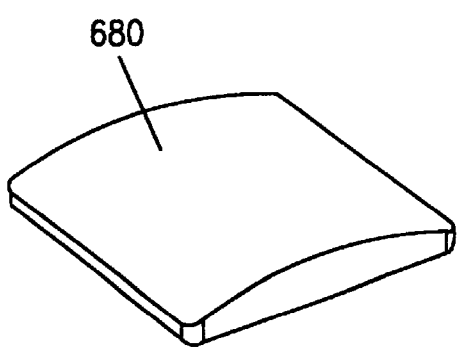
Figure 16A:
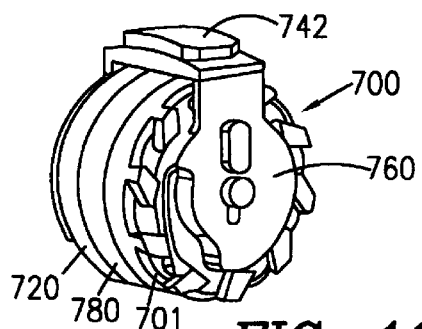
Figure 16B:
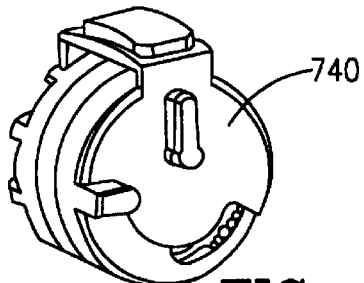
Figure 16C:
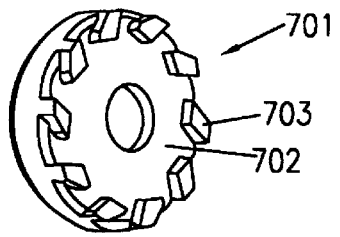
Figure 16D:
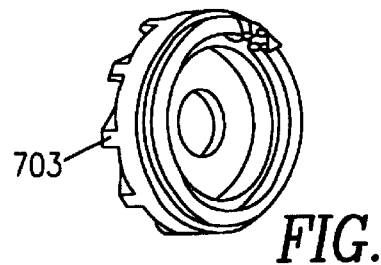
Figure 16E:
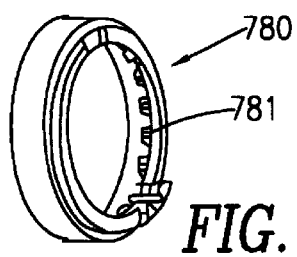
Figure 16F:
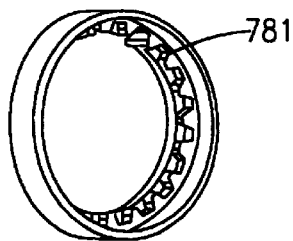
Figure 16G:
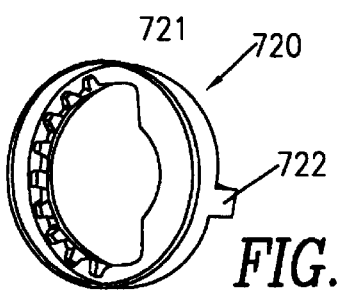
Figure 16H:
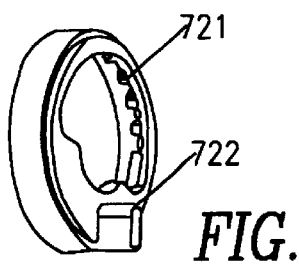
Figure 16I:
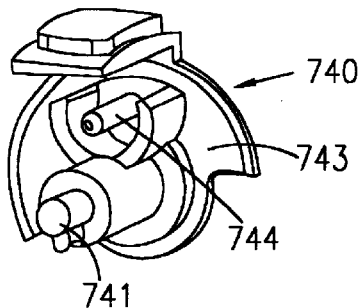
Figure 16J:
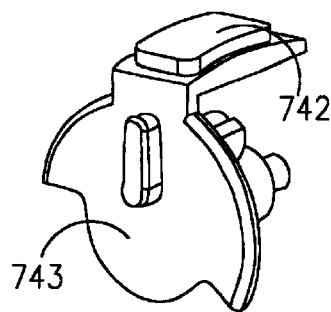
Figure 16K:
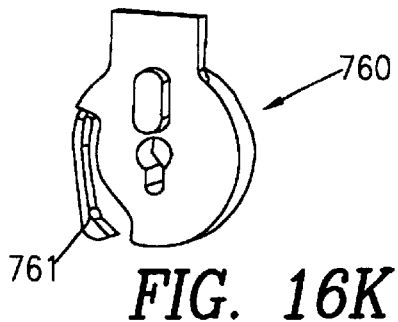
Figure 16L:
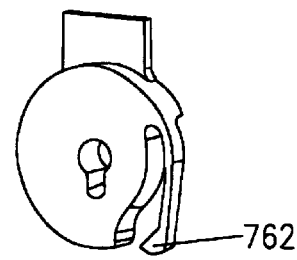
Figure 16M:
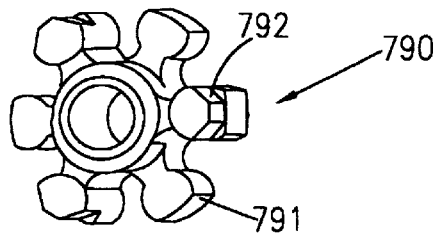
Figure 16N:
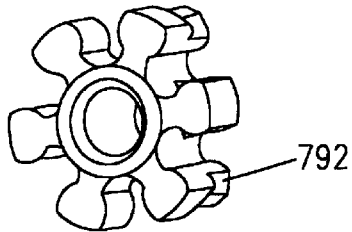
Figure 16O:
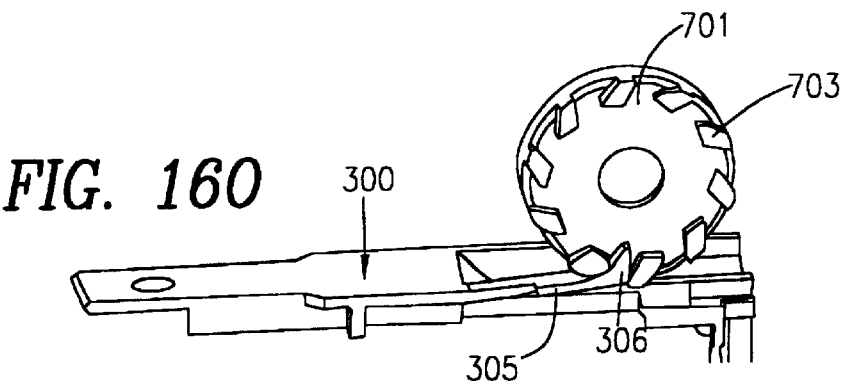
Figure 17A:
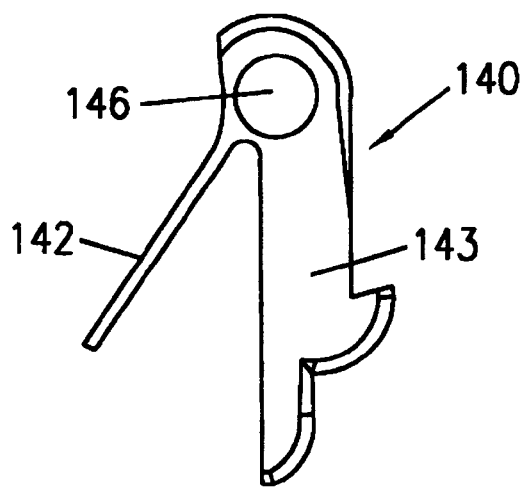
Figure 17B:
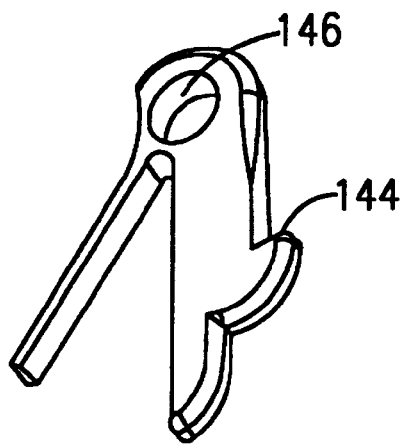
Figure 17C:
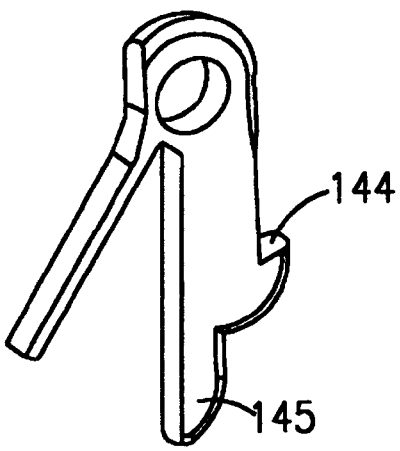
Figure 18A:
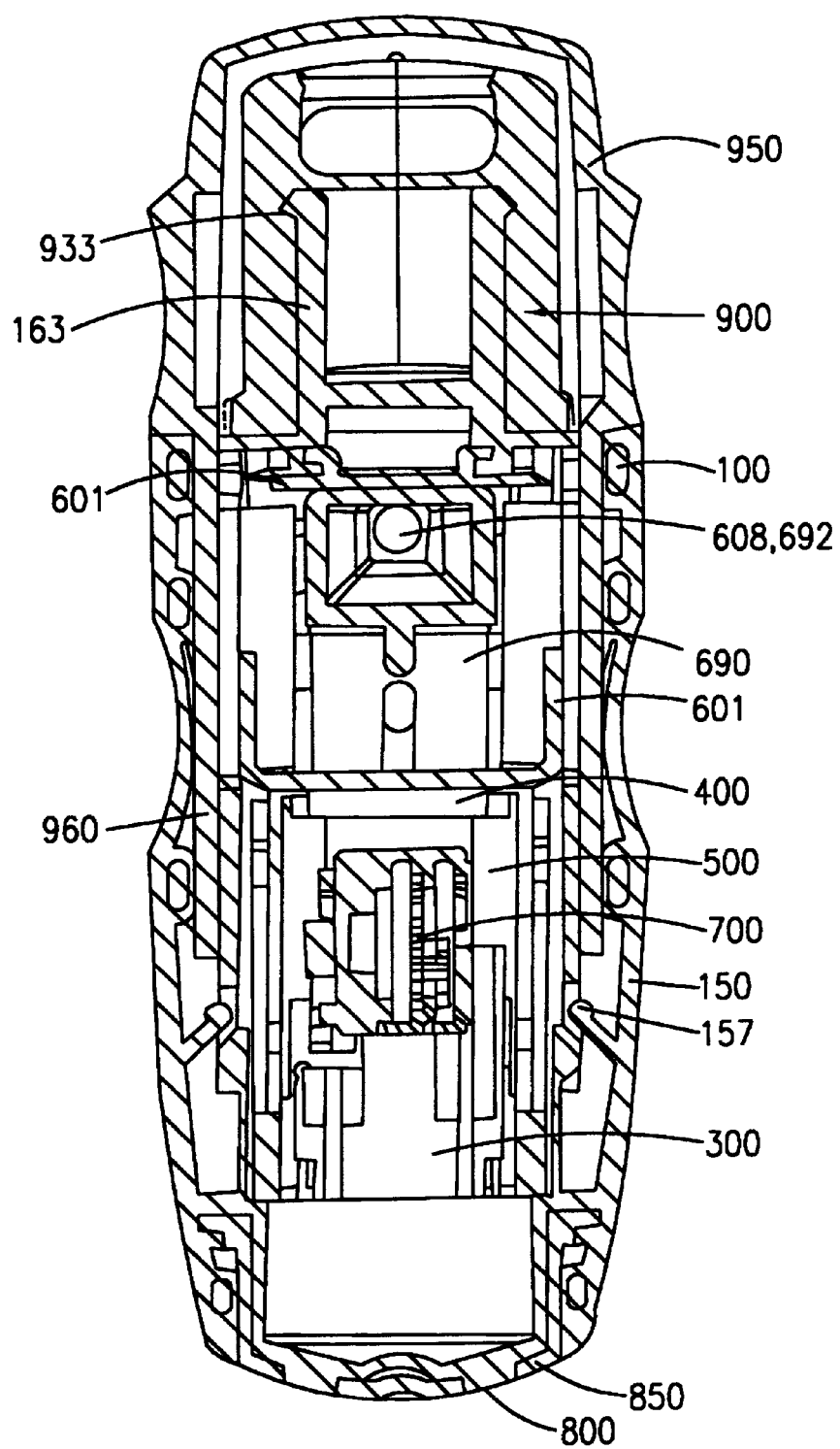
Figures 18B, 18C:
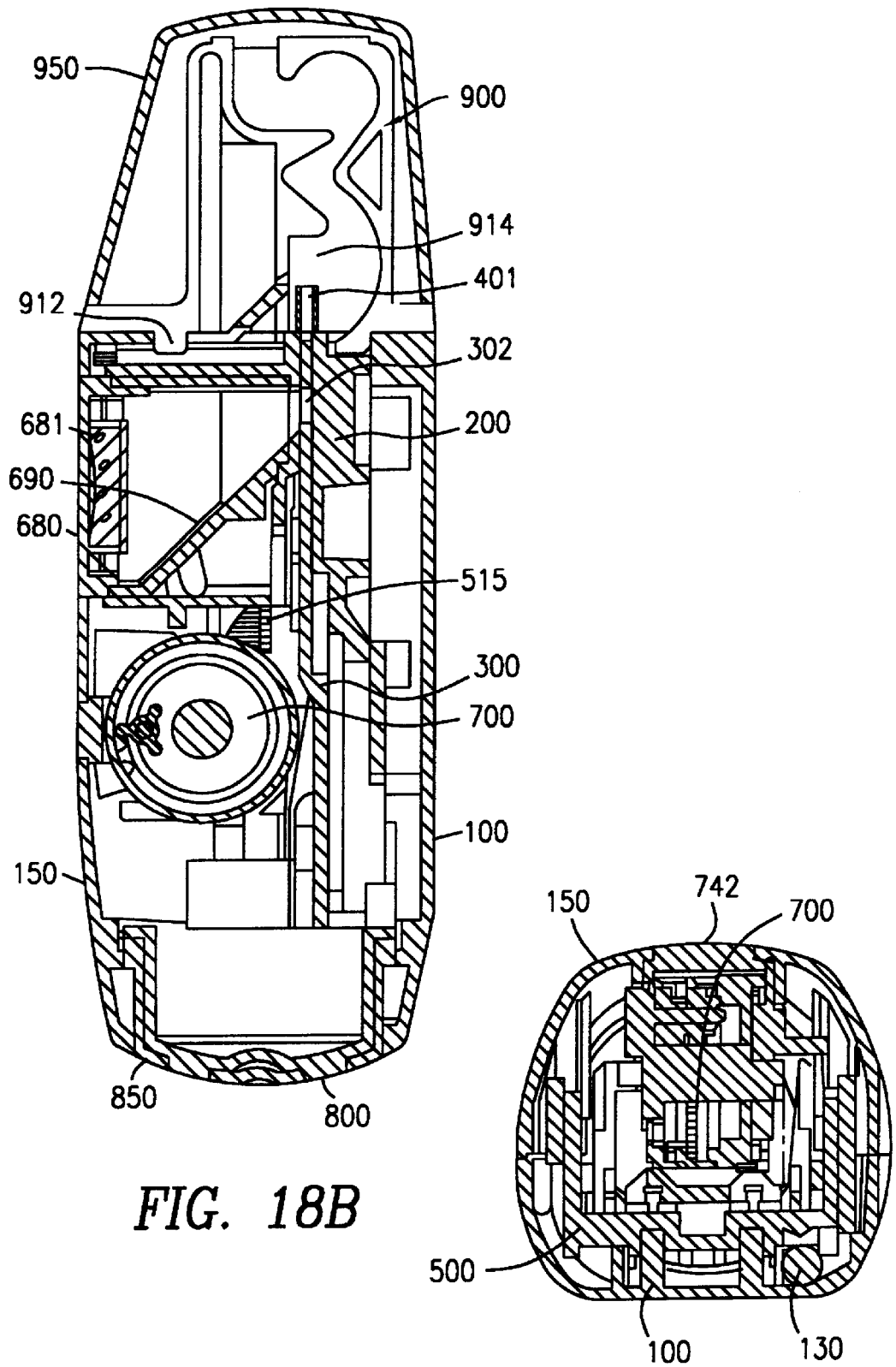
Figure 19A:
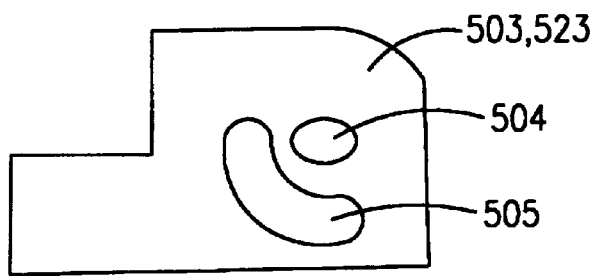
Figure 19B:
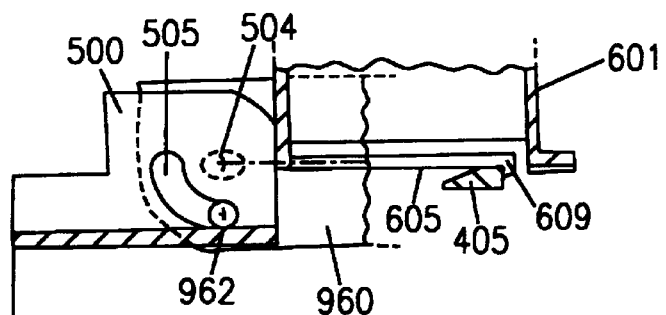
Figure 19C:
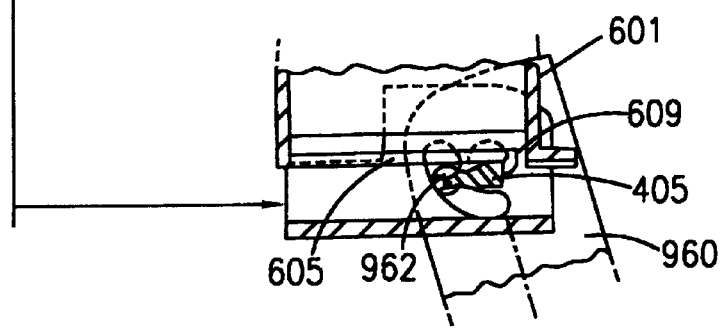
Figure 19D:
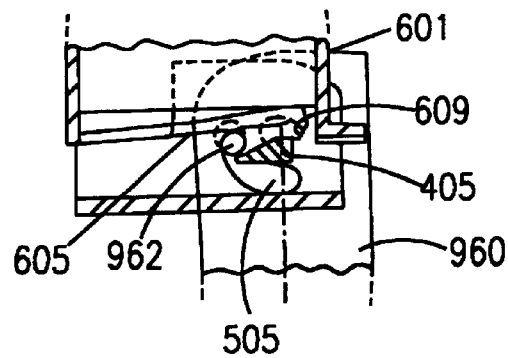
Figure 20A:
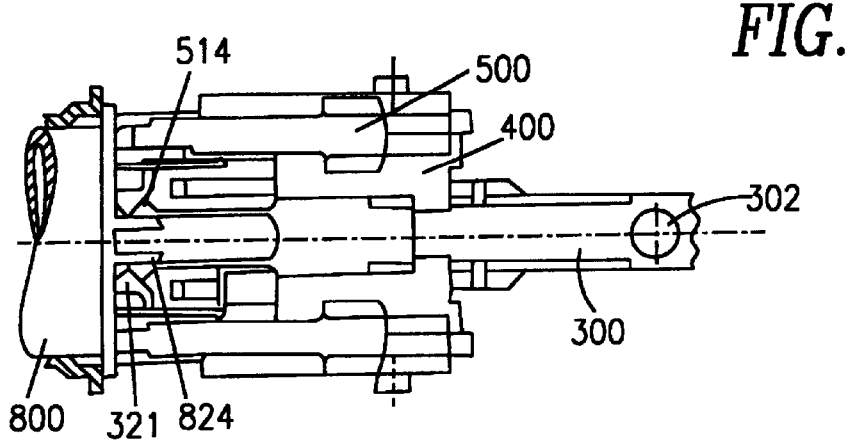
Figure 20B:
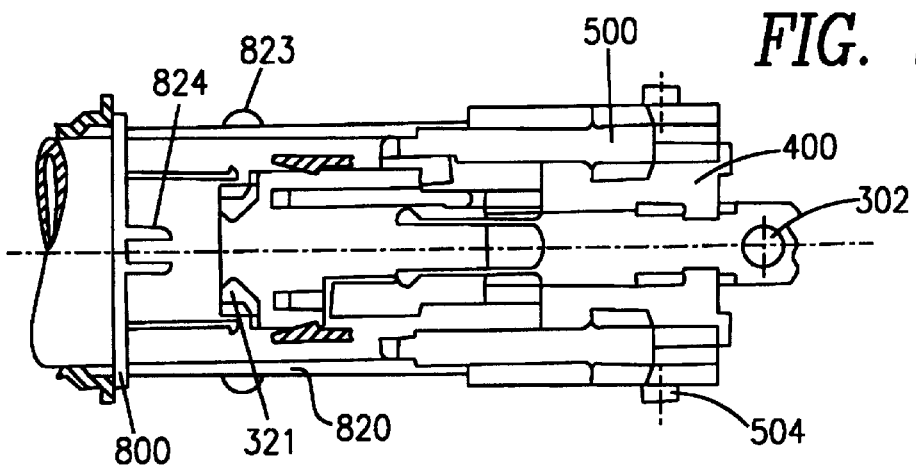
Figure 20C:
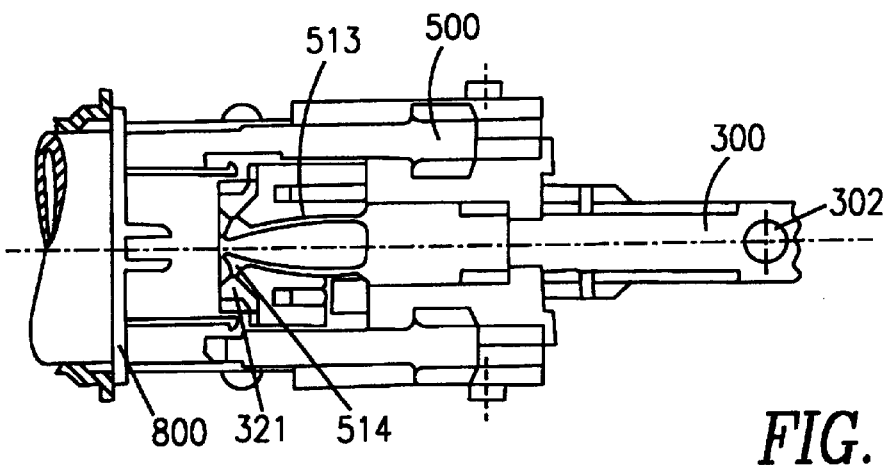
Figure 20D:
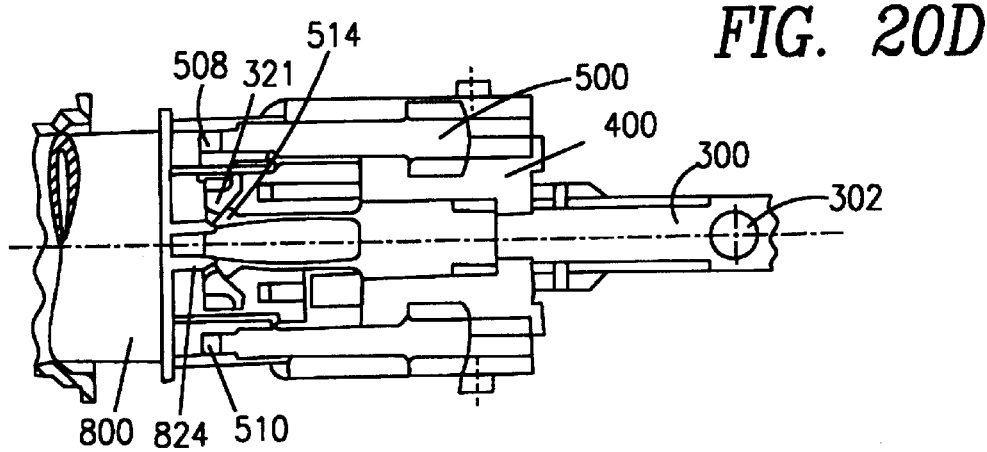
Figure 20E:
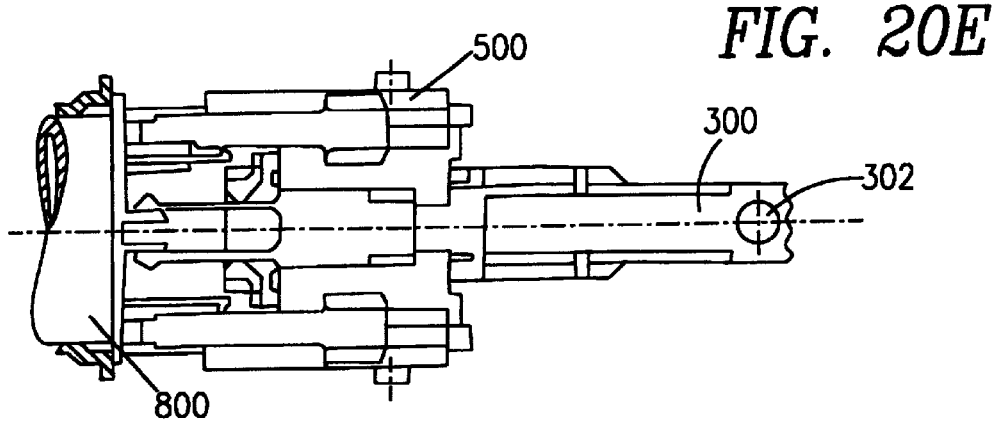
Figure 20F:
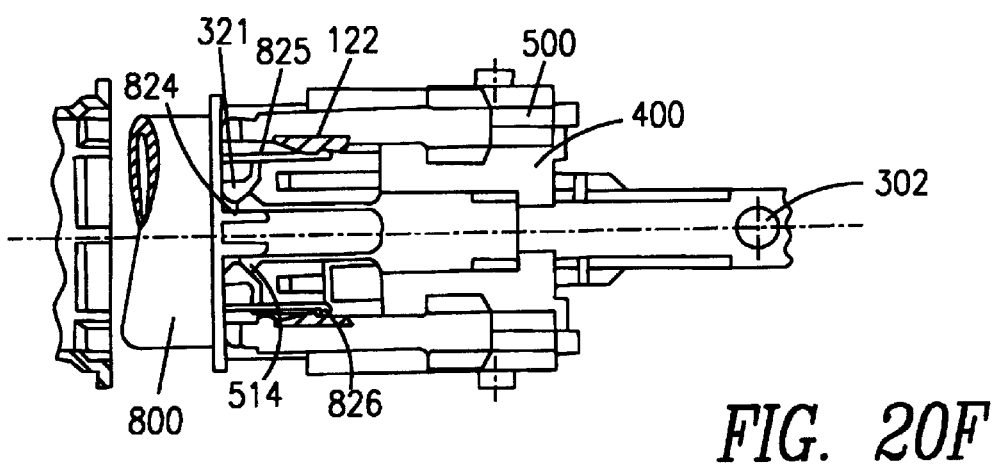
Figure 21A:
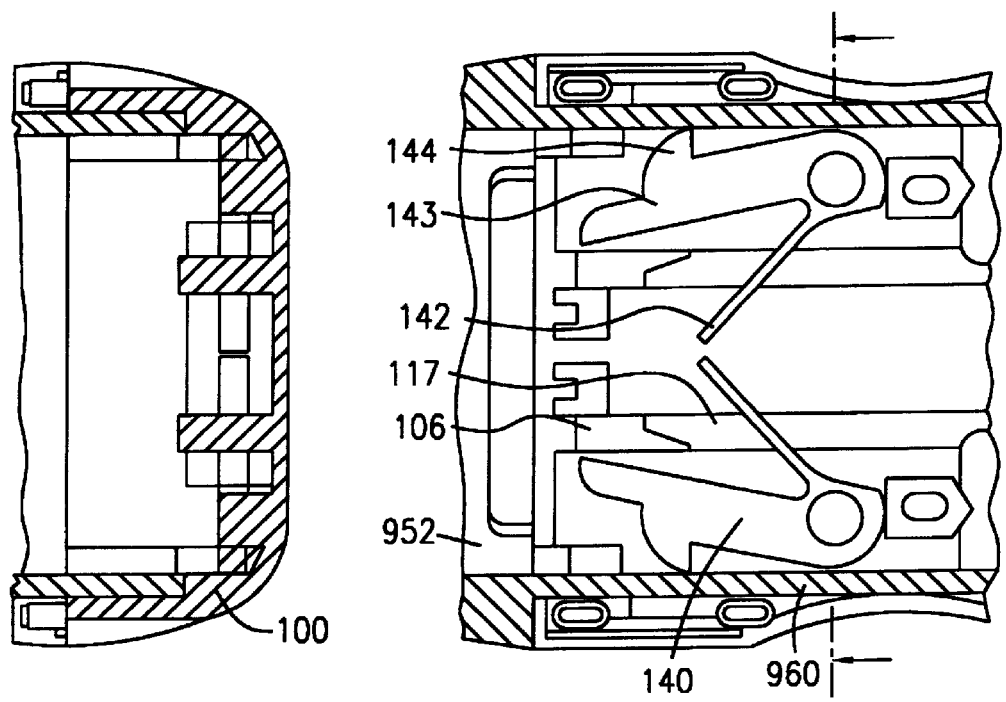
Figure 21B:
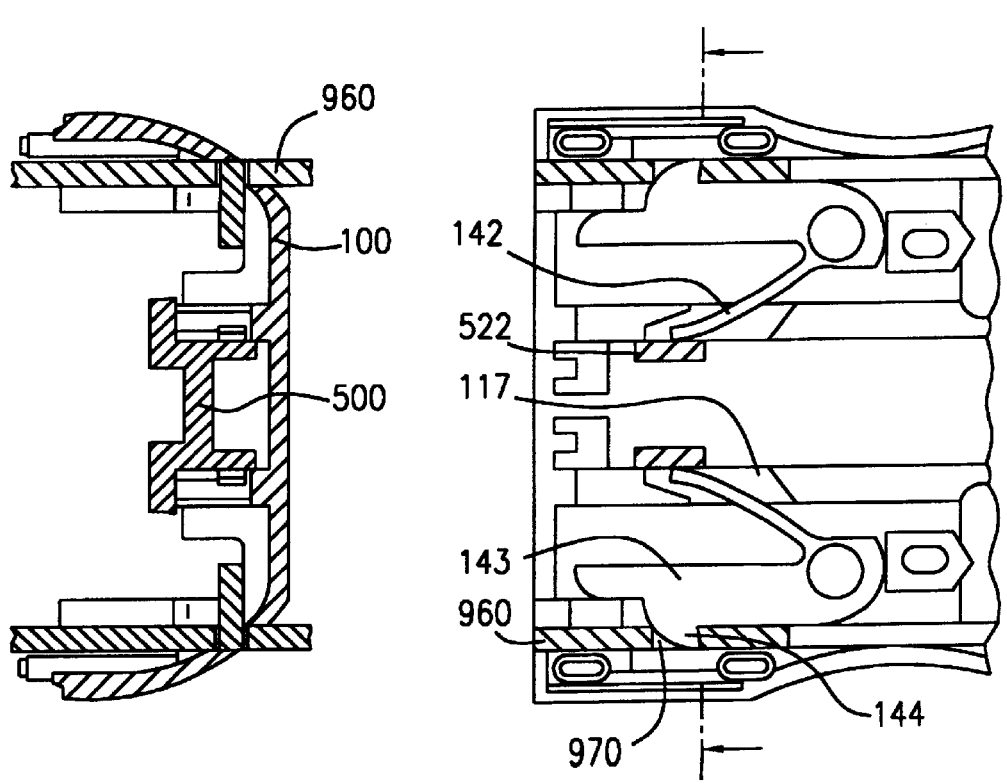
Figure 21C:
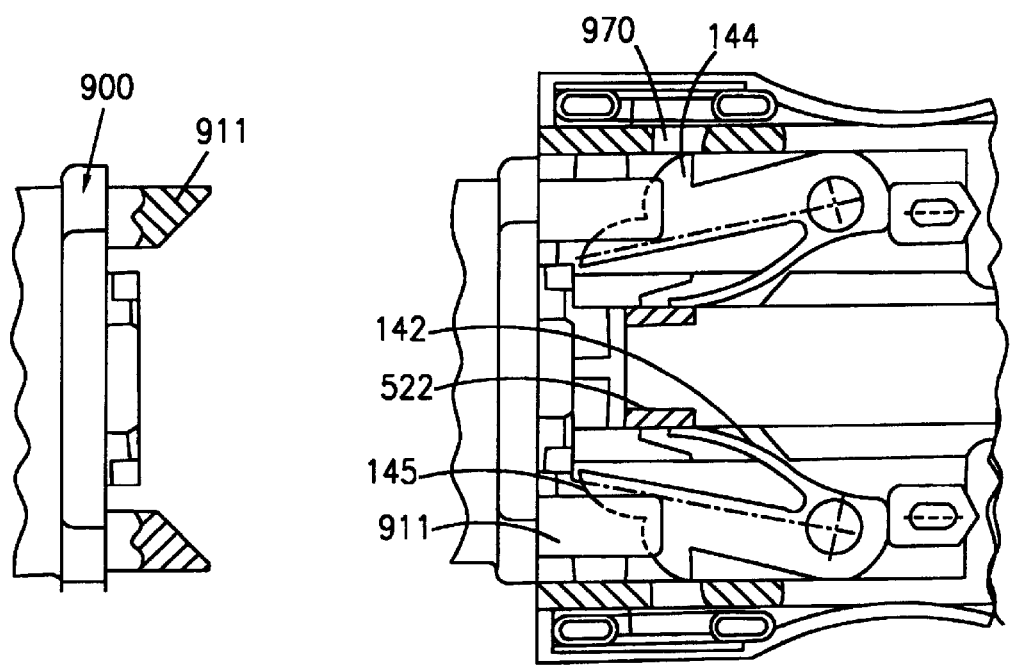
Figure 22A:
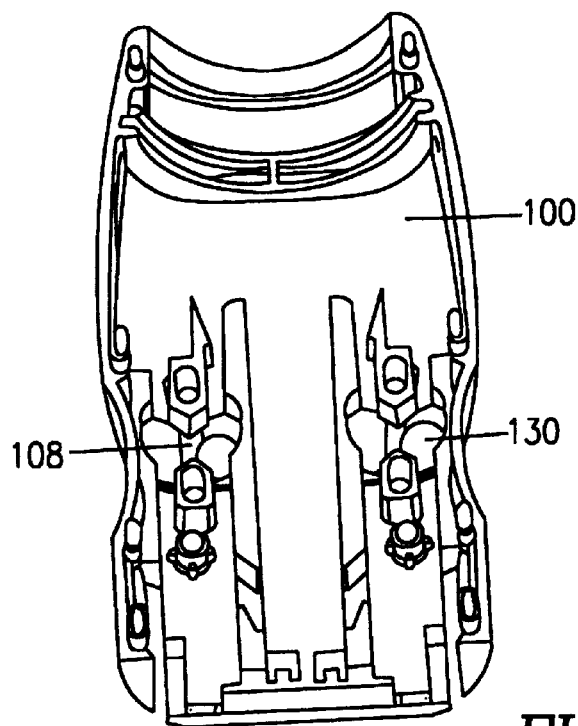
Figure 22B:
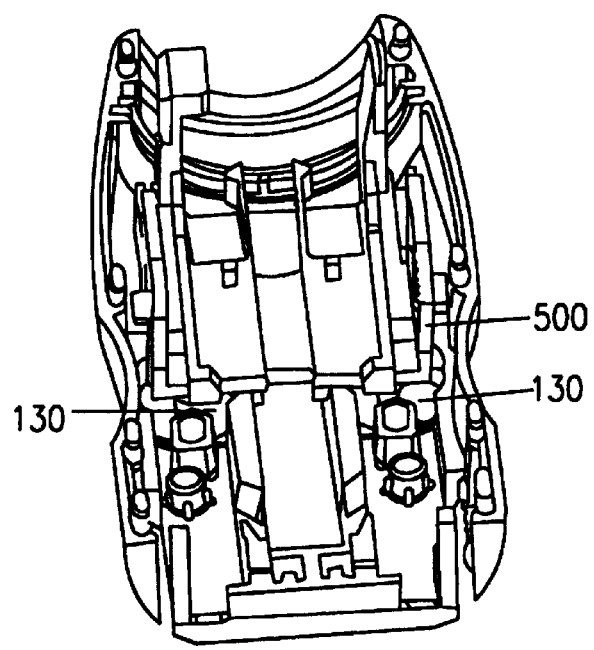
Figure 23A:
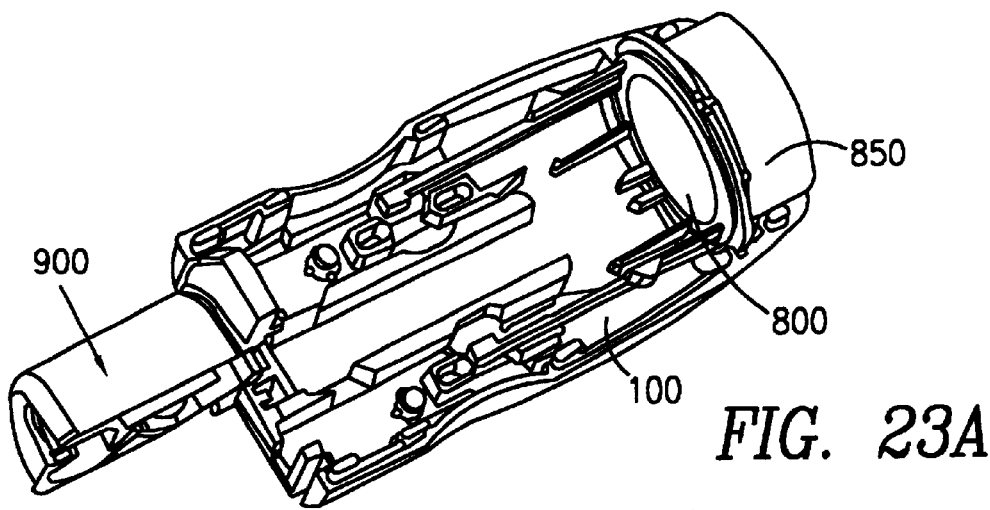
Figure 23B:
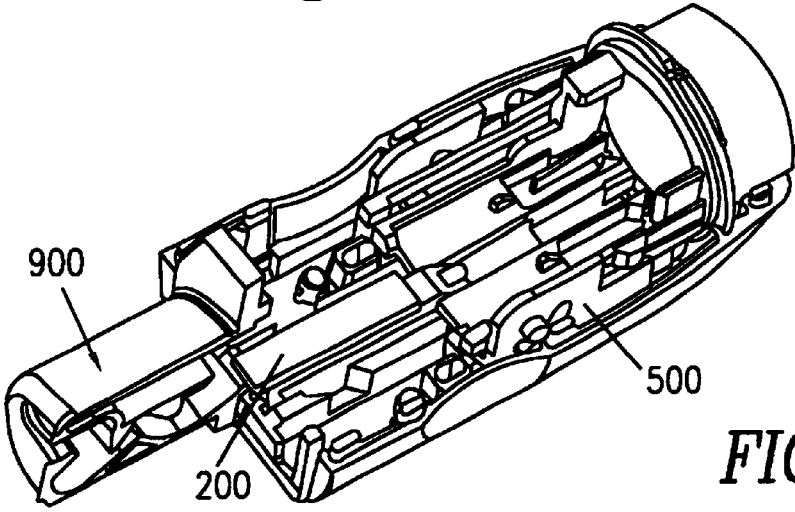
Figure 23C:
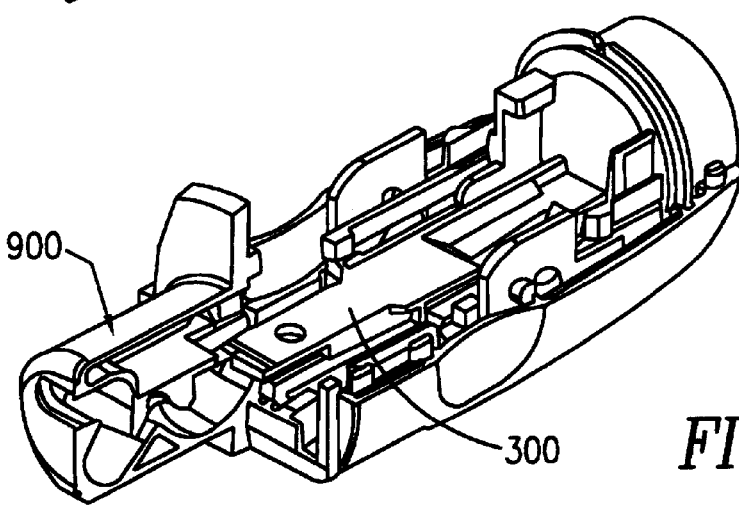
Figure 23D:
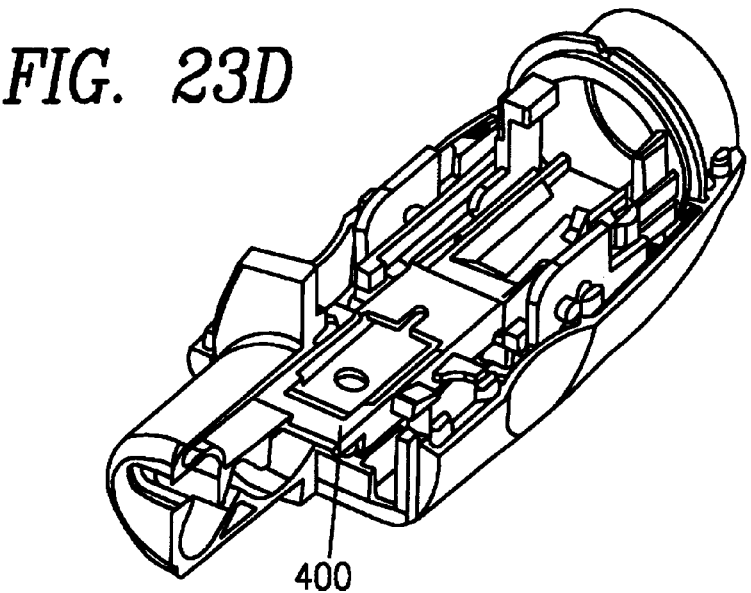
Figure 23E:
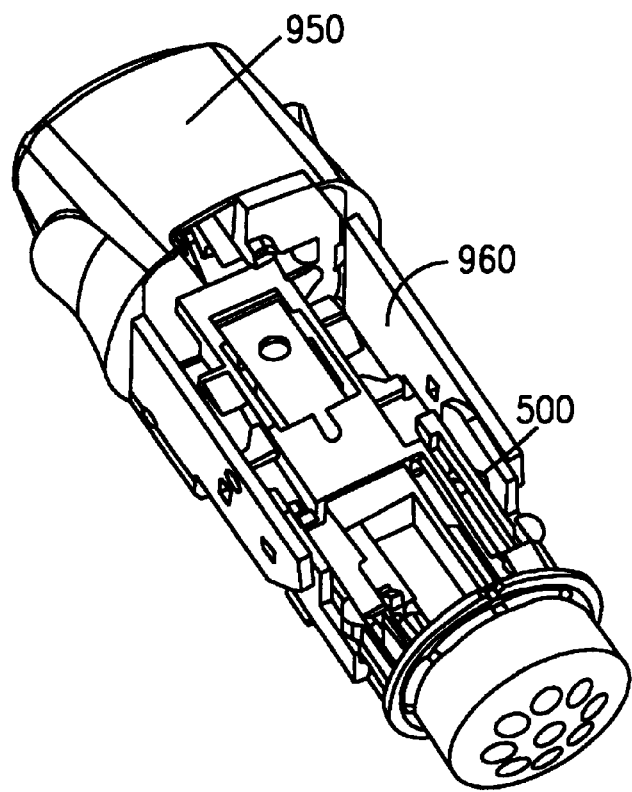
Figure 23F:
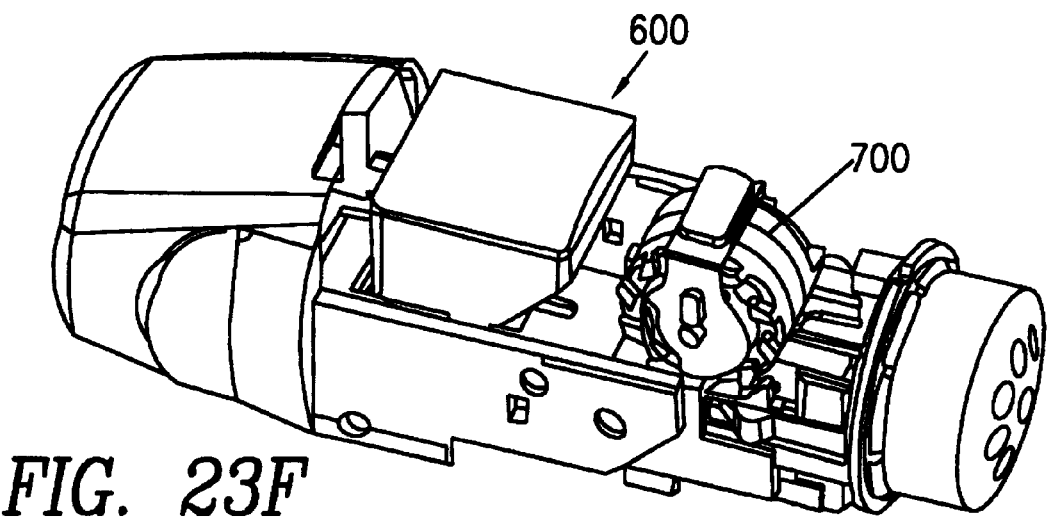
Figure 23G:
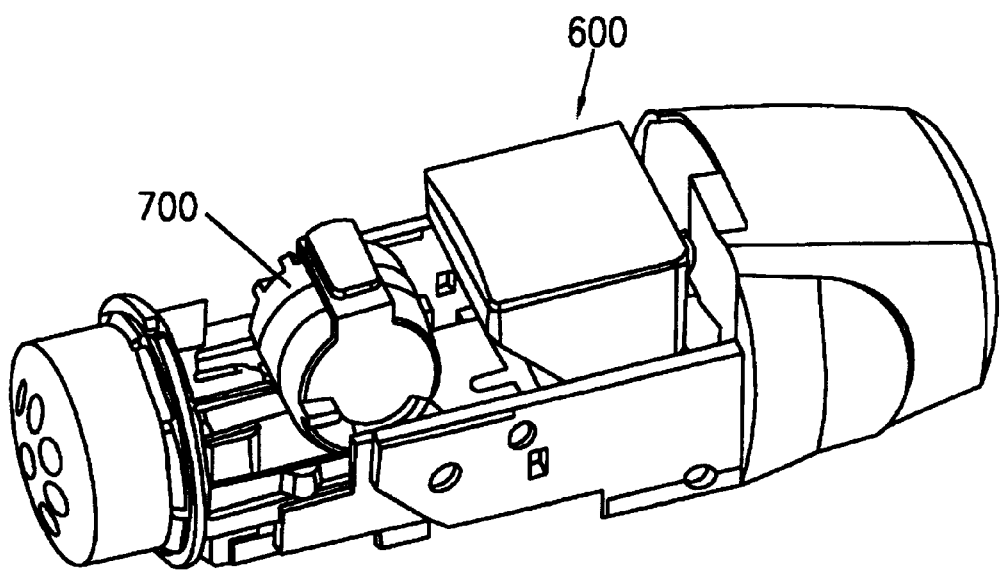

FIG. 1A inhaler, side view; closed state (starting position→situation A1);

FIG. 1B inhaler, rear view;

FIG. 1C inhaler, front view;

FIG. 1D inhaler, plan view;

FIG. 1E inhaler: protective cap pulled out (intermediate position→situation A2);

FIG. 1F inhaler: protective cap swung down fully (ready for inhalation→situation A4; inhalation omitted→situation A5; inhalation incomplete→situation A6; inhalation complete→Situation A7);

FIG. 2A protective cap, perspective view;
FIG. 2B protective cap, plan view;
FIG. 2C protective cap, side view;
FIG. 2D view into the protective cap;
FIG. 3A lower part of housing, perspective view;
FIG. 3B lower part of housing, plan view;
FIG. 3C lower part of housing, side view;
FIG. 3D lower part of housing, cross-sectional view;
FIG. 3E lower part of housing, perspective view with blocking hooks and balls;
FIG. 3F lower part of housing according to FIG. 3E, plan view;
FIG. 4 upper part of housing, perspective view;
FIG. 5A mouthpiece, perspective view of the base plate;
FIG. 5B mouthpiece, side perspective;
FIG. 5C one half of mouthpiece, external view;
FIG. 5D one half of mouthpiece, internal perspective;
FIG. 5E mouthpiece opened out, internal perspective;
FIG. 6A slide rail, perspective view from below;
FIG. 6B slide rail, side perspective;
FIG. 7A carriage, perspective view from below;
FIG. 7B carriage, perspective view from above, laterally, from the front;
FIG. 7C carriage, perspective view from above, front;
FIG. 7D carriage, perspective view from above, rear;
FIG. 8A dosing slide, perspective view from above;
FIG. 8B dosing slide, perspective view from above, rear;
FIG. 8C dosing slide, perspective view from below;
FIG. 9A shutter, perspective view from above;
FIG. 9B shutter, perspective view from below;
FIG. 10A valve shield, perspective view;
FIG. 10B valve shield, side perspective;
FIG. 11A valve guide, inner perspective;
FIG. 11B valve guide, outer perspective;
FIG. 12A funnel, perspective view from above;
FIG. 12B funnel, perspective view from below;
FIG. 13A funnel holder, perspective view from above;
FIG. 13B funnel holder, side perspective;
FIG. 13C funnel holder, perspective view from below;
FIG. 14A funnel lid, perspective view from above;
FIG. 14B funnel lid, perspective view from below;
FIG. 14C funnel lid with semi-permeable membrane;
FIG. 15A funnel holder, funnel and funnel lid, side perspective;
FIG. 15B funnel holder and fitted funnel, perspective view from above;
FIG. 16A counter, perspective view of the units wheel;
FIG. 16B counter, perspective view of the hundreds wheel;
FIG. 16C counter, units wheel, outer perspective;
FIG. 16D counter, units wheel, inner perspective;
FIG. 16E counter, tens wheel, outer perspective;
FIG. 16F counter, tens wheel, inner perspective;
FIG. 16G counter, hundreds wheel, inner perspective;
FIG. 16H counter, hundreds wheel, outer perspective;
FIG. 16I counter body, inner perspective;
FIG. 16J counter body, outer perspective;
FIG. 16K counter, cover plate, outer perspective;
FIG. 16L counter, cover plate, inner perspective;
FIG. 16M counter, drive wheel, outer perspective;
FIG. 16N counter, drive wheel, inner perspective;
FIG. 16O engagement of the dosing slide on the counter, units wheel;
FIG. 17A blocking hook, plan view;
FIG. 17B blocking hook, perspective view from right;
FIG. 17C blocking hook, perspective view from left;
FIG. 18A inhaler, horizontal longitudinal section according to FIG. 1A on line A—A;
FIG. 18B inhaler, vertical longitudinal section according to FIG. 1D on lin B—B;
FIG. 18C inhaler, vertical transverse section according to FIG. 1D on line C—C;
FIGS. 19A to 19D functioning principle of the release of the shutter;
FIG. 19A side wings of the carriage with aperture and cam;
FIG. 19B closed inhaler according to FIGS. 1A and 18A (situation A1);
FIG. 19C shutter close to release, with the protective cap not swung down fully (situation A3);
FIG. 19D shutter released, with protective cap swung down fully in accordance with FIG. 1F (situation A4);
FIGS. 20A to 20F functioning principle of the inhaler
FIG. 20A inhaler closed in accordance with FIGS. 1A, 18A and 19B (starting position→situation A1);
FIG. 20B inhaler open in accordance with FIGS. 1F and 19D (ready for inhalation→situation A4);
FIG. 20C closing the inhaler (inhalation omitted→situation A5);
FIG. 20D closing the inhaler (inhalation incomplete→situation A6);
FIG. 20E inhaler closed (after incomplete inhalation→situation A8);
FIG. 20F inhaler closed (after completed inhalation→situation A7);
FIGS. 21A to 21C functioning principle of the blocking hooks:
FIG. 21A blocking hooks fitted (starting position→situation B1);
FIG. 21B protective cap blocked when mouthpiece missing (incorrect position→situation B2);
FIG. 21C pivotable protective cap, with mouthpiece fitted (desired position→situation B3);
FIGS. 22A and 22B functioning principle of the blocking of the inhaler at an inclined position:
FIG. 22A side position of the blocking balls on incorrect positioning of the inhaler;
FIG. 22B blocked inhaler;
FIGS. 23A to 23G successive construction of inhaler, perspective views;
FIG. 23A lower part of housing with valve shield, valve guide and one mouthpiece half;
FIG. 23B representation in accordance with FIG. 23A, with slide rail and carriage added;
FIG. 23C representation according to FIG. 23B, with dosing slide added;
FIG. 23D representation in accordance with FIG. 23C, with shutter added;

FIG. 23E representation in accordance with FIG. 23D, with protective cap added, without lower part of housing;

FIG. 23F representation in accordance with FIG. 23E, with funnel holder, funnel, funnel lid and counter added; and FIG. 23G representation in accordance with FIG. 23F, from the rear side.

EXEMPLARY EMBODIMENT

In the text which follows, the inhaler according to the invention will be described in greater detail in terms of its construction, as well as its function, with reference to the attached drawings, and possible modifications are mentioned by way of conclusion.

The following statement applies to the whole of the description following. If, for the purpose of clarity of the drawing, reference numbers are included in a figure but are not explained in the directly relevant text of the description, then reference is made to their mention in preceding figure descriptions. In the interest of intelligibility, the repeated designation of components in succeeding figures is for the most part omitted if it is clear from the drawings that the components concerned are "recurring" components.

FIGS. 1A to 1D

Externally, the inhaler according to the invention is made up of the lower part 100 of the housing, the upper part 150 of the housing, and the protective cap 950. The lower part 100 of the housing and the upper part 150 of the housing have an elongate, semi-monocoque configuration. The upper part 150 has, on its top side, a fairly large opening 151 for receiving a funnel lid 680, and a window 152 through which the status of the counter can be read off. The lower part 100 of the housing and the upper part 150 of the housing are joined to one another such that a housing is obtained which is in principle closed. Grip contours 951 are provided on the outside of the protective cap 950 to permit better gripping. Grip contours, preferably designed as grip dimples 113, are also arranged on both sides of the housing, in this case extending over the lower part 100 of the housing and the upper part 150 of the housing.

On the top of the protective cap 950, towards the outer edge, there is an elongate recess, by which means a clearance 968 is created together with the adjoining upper part 150 of the housing. By looking into this clearance 968 it is possible to ascertain if the mouthpiece is fitted and the clearance 968 is thus filled, or if the mouthpiece is missing and the clearance 968 is consequently open. Opposite the protective cap 950—on the rear part of the inhaler—the perforated base 854 of the valve guide enclosed by the lower part 100 of the housing and upper part 150 of the housing can be seen.

In the closed state shown here, the starting position—subsequently referred to as Situation A1—the protective cap 950 is fitted flush with the lower part 100 of the housing and the upper part 150 of the housing. Thus, the medical preparation stored in the inhaler is protected quasi hermetically from external humidity.

FIG. 1E

The inhaler has to be opened before use; to do this, the protective cap 950 is first of all pulled out in the axial direction. The line along which the protective cap 950 is pulled out is limited by a pair of side arms 960 which are fixed on the protective cap 950 and engage in a longitudinally displaceable manner in the inside of the inhaler. With the protective cap 950 pulled out this far, the mouthpiece 900 is already partly visible and is attached to the lower part 100 of the housing and the upper part 150 of the housing at the front and is enclosed on both sides by the side arms 960. As will be explained later, this step is associated with a temporary vibration for exact dosing of the medicament from the powder reservoir. This intermediate position, with the protective cap 950 pulled out, is hereinafter referred to as Situation A2.

FIG. 1F

In order to allow the patient access to the mouthpiece 900, i.e. to permit inhalation, the protective cap 950 suspended on the side arms 960 has to be swung down in a further maneuver. The mouthpiece 900 with the mouth tube 920 protruding from the base plate 910 is now fully visible. The channel outlet 922 through which the patient inhales the medicament is situated on the end face 921 of the mouth tube 920.

In this position, with the protective cap pulled out and swung fully down—subsequently referred to as Situation A4—the inhaler itself is prepared for inhalation. The dose of medicament which has been made ready is in a loosened state. It should be understood that the protective cap 950 can only be swung down when it has first been pulled out to the limit. The dimensioning of the mouthpiece 900, the length of the side arms 960, and the sole possibility of swinging the protective cap 950 downwards, cause the patient by necessity to place the inhaler in the correct position. If the inhaler were used upside down in error, the patient would notice this immediately since his nose would hit against the protective cap 950 and he would thus barely be able to apply the mouthpiece 900.

Situation A3 characterizes the state in which the protective cap 950 is in its swing movement and has not yet reached its lowest position.

FIGS. 2A to 2D

The protective cap 950 consists of the two aforementioned side arms 960 and the actual cap 952. The clearances 968, which provide space for the base plate 910 of the mouthpiece 900, are arranged on that edge of the cap 952 facing towards the mouthpiece 900, centrally on the top side and bottom side.

The two side arms 960 each extend laterally into the cap 952. At the front part, which engages in the inhaler, the side arms 960 have a special construction symmetrical to one another. Each side arm 960 has a square, rounded aperture 961, a pin 962 lying below the rounded aperture 961 and directed inwards, a recess 963 incorporated from the underside of the side arm and having a cut edge 964, as well as forward bevels 969. Between the aperture 961 and the cut edge 964 in each side arm 960 there is a further rectangular aperture 970. Offset above this aperture 970 there is an outwardly directed dimple 971. The same type of dimple 972 is arranged in the lower area of the side arm 960 near the entry to the cap 952.

FIGS. 3A to 3D

The lower part 100 of the housing has, on both sides, a plurality of stop cams 101 spaced apart from one another and projecting above the side wall. To the rear, the lower part 100 of the housing is strengthened at the end, so that a semicircular bearing ring 102 is obtained. A double wall 103, likewise semicircular and with a radial receiving groove 104, is provided on the base at a distance from the bearing ring 102. Running centrally between the double wall 103 is a raised, axial connecting web 115.

Arranged on the base are two parallel bars 106 which extend from the front side 105 and which each have an outwardly facing indentation 116 in the rear area and an obliquely cut aperture 117 in the front area. Together with two columns 118 lying opposite one another at a distance, and a rail 119 extending along with wall of the lower part 100 of the housing, the indentation 116 delimits a depression-like ball socket 108. There is also an indentation 120 provided in the rail 119, and the indentations 116, 120 of the identical form lie opposite one another. The columns 118 have points 121 which are directed towards one another and which at their deepest point are located in the ball socket 108. On each of the rear columns 118 there is an inwardly pointing hook 122. A raised plug 123 is in each case arranged in front of the front pillars 118, facing towards the front side 105. At the front side 105, two receiving notches 109 are incorporated, as well as two axially extending longitudinal slots 110 in the base—near each housing wall. A safety cam 125 sits to the side at the entrance of each longitudinal slot 110. Between the two bars 106 and the front side 105 there are two U-shaped depressions 124.

FIGS. 3E and 3F

In the completed state, a blocking ball 130 lies in each ball socket 108 and, with the inhaler in the correct position, this blocking ball 130 is located at the deepest point between the points 121 of the columns 118. When the inhaler is in an excessively horizontal or axial inclined position, the blocking balls 130 roll into the indentation 116 of the bar 106 or into the indentation 120 of the rail 119 and effect a blocking of the inhaler, as described in FIGS. 22A and 22B.

To ensure that the removed mouthpiece 900 is put back in place before the inhaler is closed, blocking hooks 140 are optionally fitted on the plugs 123. A blocking hook 140 consists of a spring arm 142 and a lever 143 with a laterally protruding blocking tooth 144 and the catch 145 pointing to the front side 105. The spring arm 142 of the blocking hook 140 passes through the aperture 117, while the lever 143 is pressed outwards by the tensioning of the spring arm 142, so that it is blocking tooth 144 protrudes into the course of the longitudinal slot 110 where, in the completed state, the respective side arm 960 of the protective cap 900 sits. The function of the blocking hooks 140 is described in detail in FIGS. 21A to 21C.

FIG. 4

Complementing the stop cams 101, the upper part 150 of the housing has plug holes 153 on its side walls. Analogously to the lower part 100 of the housing, the upper part 150 of the housing also has a semicircular bearing ring 154 to the rear, as well as a double wall 155 with a receiving groove 156. The half bearing rings 102 and 154, respectively, and the receiving grooves 104 and 156 combine to form full circles.

On the side walls, mounted ahead of the receiving groove 156, there are in each case a support cam 158 and a higher overspring rib 157. The support cam 158 and the overspring rib 157 project towards the center of the upper part 150 of the housing and have a common point of origin on the side wall. Adjacent to the window 152, two parallel supports 159 spaced apart from one another are arranged on the interior of the upper part 150. In the interior of the upper part 150 there is also the recess 151 for the funnel which is to be fitted. On both sides of this recess 151, towards the side walls, a limit cam 164 in each case stands out from the interior of the upper part 150.

Corresponding to the longitudinal slots 110 in the lower part 100 of the housing, there are also two slots 161 in the front side 160 of the upper part 150 of the housing. In the front side 160 there is additionally a central receiving notch 162, and two elastic clamping prongs 163 extend from the front side 160 in the direction of the mouthpiece 900. A cross-piece 165 stretches between the front side 160 and the base of the clamping prongs 163, and adjacent to the receiving notch 162. To the rear of the front side 160, the clamping prongs 163 merge into a vertical U-profile 166, the vertical grooves 167 of the U-profiles 166 internally adjoining the front side 160 and facing one another.

FIGS. 5A to 5E

The mouthpiece 900 consisting of the base plate 910 and the mouth tube 920 is advantageously made of two halves which are joined together, for example, by an integral film hinge 923 provided on the end face 921. On the base plate 910, facing the inhaler, there is a full connector plug 911 at the bottom of each half, and a half-cam 912 at the top, which complements the adjacent half-cam 912. Each connector plug 911 has at its front free end, in the lower area, a recess 930 with an inwardly directed bevel 931.

Incorporated underneath the two half-cams 912 is an engagement opening 913 which extends as a shaft 932 right into the mouth tube 920. Deeper in the shaft 932, a recessed groove 933 is present in each case laterally in the wall of the mouth tube 920. The channel inlet 914 for the atomizer path 924 of the mouth tube 920 lies below the engagement opening 913. The channel inlet 914 is connected to the channel outlet 922 via the atomizer path 924. A horizontal ramp 935, complementing the second half of the mouthpiece, is in each case arranged on the base plate 910 under the channel inlet 914.

Inside the atomizer path 924, behind the channel inlet 914, there are a plurality of baffles 925 which protrude into the atomizer path 924 for impacting the medicament-containing air stream and causing it to swirl, so that the atomizer path 924 acquires a course which is rich in curves. Nearer the channel outlet 922, the powder aerosol flowing through enters via an S-curve into an enlarged channel section 928 and is here deflected to the channel outlet 922. The purpose of the special configuration of the atomizer path is to deagglomerate the powder and to reduce the flow rate of the powder so as to deposit coarser particles which are ineffective for inhalation. At the same time, the impacting of particles of active substance in the pharynx of the patient is thus prevented. The mouth tube 920 is flattened off horizontally, at least in the area of the end face 921, so that the patient is induced to employ the correct positioning of the inhaler during use.

FIGS. 6A and 6B

The slide rail 200 has two longitudinal grooves 202 which extend laterally from the end face 201 and parallel to one another, and which reach to approximately halfway along the slide rail 200. In a continuation of the end face 201, two feet 204 spaced apart from one another extend downwards from the bottom of the slide rail 200. At the top, the slide rail 200 has a ledge-like roof part 210 which protrudes over the end face 201 in the matter of a projecting roof. At the opposite end from the end face 201, the slide rail 200 ends in a sloping surface 205 which merges ramp-like with the top surface of the slide rail 200, the roof part 210 ending in front of the sloping surface 205.

FIGS. 7A to 7D

The carriage 500 has two wings 503, 523 rising laterally and beginning on the front side 501, with an outwardly directed cam 504 being in each case arranged thereon. The cam 504 is wider in the horizontal than in the vertical, so that an approximately oval shape is obtained. An arcuate aperture 505 is incorporated in the wings 503, 523 and runs round the cam 504 from below in a part circle. At its rear side 507, the carriage 500 has two laterally rising struts 508, 510, the strut 508 having a horizontal shoulder 509. Two pull cams 512 rise from the carriage base 511, while to the rear side 507 the carriage base 511 continues in the form of two elastic spring tongues 513 which end as spring wedges 514 and can be deflected out to the sides. Between the two spring tongues 513, a longitudinal groove 520 extends centrally through the carriage base 511. A pull catch 521 is present on the front side 501 between the groove 520 and each of the wings 503, 523. Towards the front side 501, the wing 523 has a grate section 515 on the inside.

Underneath the groove 520, the carriage 500 has two runners 522 on its underside. Also on the underside of the carriage, towards the outside as viewed from the runners 522, there are two pairs of impact ridges 524 which correspond to the two ball sockets 108 in the lower part 100 of the housing. The two impact ridges 524 on one pair are arranged at a distance from one another. A stepped bulge 516 is positioned ahead of each pair of impact ridges 524, in the direction of the front side 501.

FIGS. 8A to 8C

Near its front edge 301, the tongue-like dosing slide 300 has a through-bore, the dosing cavity 302. Starting from the front edge 301, the dosing slide 300 extends firstly as a narrow tongue tip 303 and then widens to the rear part 304. A spring leaf 305, from which a cam 306 rises perpendicularly, is arranged on the outside flank of the rear part 304.

On the underside, the dosing slide 300 has flank ridges 307 which begin immediately behind the dosing cavity 302 and there form limit stop edges 308. The dosing cavity 302 is surrounded by a radial sealing rim 320 on the underside. Near the transition to the rear part 304, there are two downwardly extending transverse cams 309. On the rear edge 310 of the dosing slide 300 there are two downwardly directed, profiled catches 321.

FIGS. 9A and 9B

The shutter 400 has the function of releasing the medicament made ready in the dosing cavity 302 only when there is a suitably forceful inhalation. At the very front, the shutter 400 has a sleeve-like closure part 401 with the through-opening 402. Behind the closure part 401 there are outer, vertical side ridges 403, beginning with a limit stop 404. An outwardly directed and ramp-shaped wing 405 is arranged on each side ridge 403. In the direction of the rear part 406, the wing 405 is followed by a side bracket 407. At the bottom, on the rear edge 408, the shutter 400 also has an outwardly directed carrier 409. On the bottom, in the area of the wings 405, two base plates 410 extend towards one another, leaving a through-gap 411. Towards the rear edge 408, the end of the rear part 406 is provided with a cover 420 which at the top stretches across the two parallel side ridges 403 and begins approximately in the area of the side brackets 407. In the cover 420 there is a rounded-off groove 421 which extends along the middle and which is open to the center of the shutter 400.

FIGS. 10A and 10B

The valve shield 800 has the function of inducing the patient to generate a defined minimum suction for a correct inhalation. The valve shield 800 consists of a cylindrical capsule 810 and a plurality of arms attached thereto and having different tasks. The capsule 810 has a flange-like collar 811 surrounding the opening and protruding outwards. The bottom 812 of the capsule 810 is convexly curved outwards and has a large number of raised stubs 813 on the outside.

The further elements of the valve shield 800 are attached perpendicularly onto the collar 811 and extend in the axial direction. On the collar 811 there is firstly a pair of long tentacles 820 which lie opposite one another and which have carriers 821 at their very front. Before the tentacles 820 there are two shorter spring arms 822 with outwardly directed wedge profiles 823 at their tips. Behind the tentacles 820 there are two further spring arms 825 with outwardly directed hooks 826. Between these spring arms 825 there are two short locking teeth 824 standing close to one another.

FIGS. 11A and 11B

The capsule-shaped valve guide 850, when fitted into the lower part 100 of the housing and the upper part 150 of the housing, serves to receive the valve shield 800, i.e. its capsule 810. To this extent the valve guide 850 has the function of a slide bearing. Complementing the collar 811 of the valve shield 800, the valve guide 850 has an external limit stop flange 851. Slide ribs 852 in the inside of the valve guide 850 have the purpose of reducing the friction as the valve shield 800 travels out. The perforated bottom 854 has numerous holes 855, so that the stubs 813 of the valve shield 800 find space therein. At the top and bottom of the limit stop flange 851 there are two diametrically opposite notches 856. The holes 855 and the stubs 813 make it possible to design the inhaler virtually closed at the rear and thus to prevent the penetration of dirt particles and the inadvertent displacement of the valve shield 800.

FIGS. 12A and 12B

The funnel 690 is intended for fitting into the funnel holder 601 (see FIGS. 13A, 13B). The funnel bottom 691 is designed sloping obliquely towards the outlet 692, so that the medicament powder flows in a favorable manner. The outlet 692 is surrounded on the outside by a sealing element 694. On the outside, the funnel 690 has retainer cams 695 projecting upwards on two opposite sides, as well as a centrally positioned fixing nose 696 which sits on the oblique funnel bottom between the retainer cams 695.

FIGS. 13A and 13B

The box-shaped funnel holder 601 has, on the underside, the holder bottom 603, the front wall 611, the rear wall 612, and the two half-height side walls 613, 614 lying between the front and rear walls 611, 612. Located in the holder bottom 603 are the funnel outlet 608 and an elongate groove 615. At the very bottom, a sealing member 622 surrounds the funnel outlet 608, so that it is possible to prevent the entry of humidity and the escape of powder from the funnel 690 onto the sliding surfaces of the dosing slide 300.

Arranged perpendicularly on the front wall 611 are two angled rails 616, and at the top of the rear wall 612 there is a support edge 602, from which a spring arm 617 in each case extends along the two side walls 613, 614. A groove 618 facing the respective side wall 613, 614 is provided in each of the spring arms 617. The side walls 613, 614 each have a downwardly open notch 619 approximately at their center on the lower edge. A grate section 621 is provided on one side wall 613 near the rear wall 612. Two elastic lamellae 605 are connected to the rear wall 612 and extend along the outer flanks of the holder bottom 603. The lamellae 605 have vertically movable ends with downwardly projecting blocking cams 609.

FIGS. 14A to 14C

The funnel lid 680 serves to close the funnel 690. On the underside of the funnel lid 680 there is a chamber 681 which is closed by a semi-permeable membrane 682. The chamber 681 is intended to receive a moisture-attracting desiccant powder and the moisture can diffuse through the semi-permeable membrane 682.

FIGS. 15A and 15B

When the funnel arrangement is in its completed state, the funnel 690 is fitted into the funnel holder 601, and the funnel 690 is closed by the funnel lid 680. However, the sequence of assembly of the inhaler need not include the prior completion of the funnel arrangement.

FIGS. 16A and 16B

The complete counter 700 consists of the units wheel 701, the tens wheel 780, the hundreds wheel 720, the counter body 740, the counter cover plate 760, and two identical drive wheels, which are not shown here. The purpose of the counter 700 is to register the number of doses used or doses still available and to indicate to the patient the inhalation which has just taken place, as long as it was performed correctly. Numbers and, if appropriate, a color marking are provided on the circumference of the counter wheels 701, 780 and 720 fixed on the axle 741 of the counter body 740. The current status of the counter is displayed under a lens 742 which sits in the window 152 of the upper part 150 of the housing. The lens 742 is connected to the counter body 740.

FIGS. 16C and 16D

The units wheel 701 has ten radially distributed cams 703 on its outer surface 702.

FIGS. 16E and 16F

The tens wheel 780 with its inner toothed ring 781 is itself of a conventional construction.

FIGS. 16G and 16H

The hundreds wheel 720 likewise has an inner toothed ring 721 and an outwardly protruding end cam 722.

FIGS. 16I and 16J

The counter body 740 consists of the base plate 743, the lens 742 set on the top at right angles, the axle 741 extending perpendicularly from the base plate 743, as well as the drive-wheel bearing 744.

FIGS. 16K and 16L

Bearing on the units wheel 701, the counter cover plate 760 is fixed on the axle 741 of the counter body 740. The counter cover plate 760 has an elastic adjusting tongue 761 with a wedge cam 762 at the end, which cam 762 moves at all times between two cams 703 of the units wheel 701.

FIGS. 16M and 16N

The star-shaped drive wheel 790 is fitted on the one hand between the units wheel 701 and the tens wheel 780 and on the other hand between the tens wheel 780 and the hundreds wheel 720. It has six uniformly arranged teeth 791, of which every second tooth 791 has an undercut 792 at its tip on one side of the drive wheel 790.

FIG. 16O

When a correct inhalation has been completed and the inhaler has been closed again by swinging the protective cap 950 upwards and pushing it in, the actuation of the counter 700 takes place. Only on pushing the dosing slide 300 back into the starting position—Situation A1—is a cam 703 on the units wheel 701 gripped by the cam 306 situation on the spring leaf 305, and the units wheel 701 thereby turned by one count position.

When the intended number of doses have been taken from the inhaler, the hundreds wheel 720 is in such a position that the end cam 722 has positioned itself at the far top and, on pulling the carriage 500 out, the shoulder 509 (see FIGS. 7A to 7D) strikes against the end cam 722. Further actuation of the inhaler is thus blocked.

FIGS. 17A to 17C

As an option for increasing the safety of handling of the inhaler, two rotationally movable blocking hooks 140 are provided which can be fastened onto the plugs 123 in the lower part 100 of the housing. The blocking hook 140 is two-armed and is divided into a thin spring arm 142 and a more solid lever 143, the spring arm 142 spreading away from the lever 143. The blocking hook 140 has a bore 146 so that the blocking hook 140 can be fastened onto the plug 123. On the lever 143 there is a blocking tooth 144 protruding out to one side and pointing away from the spring arm 142, as well as a catch 145 pointing forwards and extending the length of the lever 143.

FIGS. 18A to 18C

In the assembled state, the following arrangement obtains in Situation A1. The lower part 100 of the housing and the upper part 150 of the housing are joined together. The mouthpiece 900 is inserted from the front and the protective cap 950 is fully closed.

The slide rail 200, the carriage 500, the dosing slide 300, the shutter 400 lie in the housing parts 100, 150. The valve guide 850 is fitted, and therein the valve shield 800, as well as the complete funnel arrangement—consisting of funnel 690, funnel holder 601 and funnel lid 680—and the counter 700. The valve shield 800 is in its rearmost position, and the dosing slide 300 is located such that the dosing cavity 302, positioned under the funnel outlet 608, can fill with medicament. The closure part 401 of the shutter 400 protrudes into the channel inlet 914. The clamping prongs 163—additionally fixing the mouthpiece 900—sit in its shaft 932 and engage in the grooves 933. The half-cams 912 of the mouthpiece 900, joined together, are locked in the receiving notch 162 in the upper part 150 of the housing. The connector plugs 911 of the mouthpiece 900 pass through the receiving notches 109 in the lower part 100 of the housing, and the ramp 935 of the mouthpiece 900 engages under the front edge of the roof part 210 of the slide rail 200. The side arms 960 of the protective cap 950 protrude through the slots 110 in the lower part 100 of the housing and through the slots 161 in the upper part 150 of the housing and embrace the wings 503, 523 of the carriage 500. The pins 962 now hang in the apertures 505, while the cams 504 engage in the apertures 961. To fix the protective cap 950 in the starting position, the safety cams 125 are locked into the dimples 972.

The feet 204 of the slide rail 200 engage in the depressions 124 in the lower part 100 of the housing. The angled rails 616 of the funnel holder 601 are driven into the vertical grooves 167 of the U-profiles 166 on the upper part 150 of the housing. The funnel 690 sits with its retainer cams 695 and its fixing nose 696 in the notches 619 and in the groove 615, respectively, of the funnel holder 601. The outlet 692 of the funnel 690 with the sealing member 694 is situated in the funnel outlet 608. In addition, the funnel holder 601 is fixed laterally by the limit cams 164 in the upper part 150 of the housing.

The complete counter 700 is held by the supports 159 in the upper part 150 of the housing. The capsule 810 of the valve shield 800 sits to the maximum extent in the valve guide 850, the limit stop flange 851 of the latter sitting in the receiving grooves 104, 156 of the lower part 100 of the housing and the upper part 150 of the housing, respectively, and the connecting web 115 coming into engagement with the notch 856.

FIGS. 19A to 19D

This sequence of figures illustrates the release of the shutter 400 which surrounds the dosing cavity 302 of the dosing slide 300 filled with medicament, upon swinging the protective cap 950 down.

FIGS. 19A and 19B

In accordance with Situation A1, the carriage 500 is so positioned that its wings 503, 523 stand before the funnel holder 601, i.e. the pin 962 of the side arm 960 of the protective cap 950, engaging in the aperture 505, is ineffective as regards unlocking the unmovable shutter 400. The blocking cams 609 under the funnel holder 601 engage behind the wings 405 projecting laterally on the shutter 400.

The dosing cavity 302 is situated underneath the funnel outlet 608 and could already be filled with medicament.
FIG. 19C The protective cap 950 has in the meantime been pulled out completely and the carriage 500 hanging on the side arms 960 has been pulled forward; Situation A2 has been reached. The shutter 400 is still unmovable and, with its closure part 401, surrounds the dosing cavity 302 which has been pushed into the channel inlet 914 of the mouthpiece 900 by means of pulling off the protective cap 950 and filled with medicament.

The swinging-down of the protective cap 950 now commenced, i.e. situation A3 is being implemented. However, the protective cap 950 has not yet been sung down fully, so that the pin 962 ascends in the aperture 505 during the swinging-down movement and consequently gradually raises and unlocks the lamella 605 arresting the shutter 400.
FIG. 19D In situation A3 which has been reached—this also applies to Situations A4 to A7—the protective cap 950 has been swung down fully, as a result of which the pin 962 forces the lamella 605 up. The blocking cam 609 is thus disengaged from the wing 405 on the shutter 400. The shutter 400 is movable, i.e. readiness for inhalation exists in conjunction with situation A3. The swung-down protective cap 950 is fixed in this position by the cooperation of the safety cams 125 in the lower part 100 of the housing and the dimples 971 on the side arms 960.
FIGS. 20A to 20F This sequence of figures illustrates a complete inhalation cycle with the mechanical events occurring in the different possible situations.
FIG. 20A In situation A1, the valve shield 800, the carriage 500 and the shutter 400 are located in their rear end position. This is the state of the inhaler after the protective cap 950 is closed following a correctly performed inhalation or prior to the first use. With the protective cap 950 being pushed in, the shutter 400, the valve shield 800 and the dosing slide 300 have been pushed back into the rear end position by the carriage 500. The pull catch 521 of the carriage 500 grips the carrier 409 of the shutter 400. With its spring wedges 514, the carriage 500 presses against the catches 321 of the dosing slide 300, the spring wedges 514 being enclosed to the inside by the locking teeth 824.

The two struts 508, 510 of the carriage 500 have pushed the valve shield 800 into its starting position. A cam 703 on the units wheel 701 of the counter 700 has been put forward one unit by the cam 306 on the dosing slide 300. The dosing cavity 302 is now once again situated underneath the funnel outlet 608.
FIG. 20B In situation A4 the inhaler is in a state of readiness for inhalation. By pulling the protective cap 950 out, the valve shield 800 is advanced from the rearmost position. The carriers 821 on the tentacles 820 have been gripped by the wings 503, 523 and pulled forward slightly, so that the stubs 813 of the valve shield 800 are removed from the holes 855 of the valve guide 850 and create air gaps. The inhaling patient is able to draw breath through these air gaps if no other air inlets are provided on the inhaler. On pulling the protective cap 950 out, the carriage 500 was moved with its grate section 515 past the grate section 621 of the funnel holder, so that a vibration was generated for promoting the flow of the medicament powder from the funnel 690 into the dosing cavity 302. The grate sections 515, 621 are dimensioned and arranged in such a way that when pulling the protective cap 950 out, vibrations are generated only so long as the dosing cavity 302 is situated under the funnel outlet 608. When the carriage 500 begins to pull the dosing slide 300 with it, the grate sections 515 and 621 disengage.

The dosing slide 300 was furthermore gripped via the transverse cams 309 by the pull cams 512 of the carriage 500 and moved forwards in the direction of the mouthpiece 900 to such an extent that the dosing cavity 302 is now surrounded by the closure part 401 of the shutter 400. The shutter 400 is also released, since the blocking cams 609 underneath the funnel holder 601 have lifted from the wings 405 of the shutter 400 as the protective cap 950 swings down. The wedge profiles 823 of the spring arms 822 of the valve shield 800 stand adjacent to the overspring ribs 157 of the upper part 150 of the housing.

Pressure is exerted from above the spring arms 617 of the funnel holder 601 so that all the components lying below are subjected to a certain amount of surface pressure. This increases the tightness and prevents the escape of medicament powder. After the protective cap 950 has been swung down, the inhaler is in a state of readiness for inhalation, and the easier mobility of the shutter 400 is now desired. When the side arms 960 are swung down, the surface pressure acting from above is in part compensated, as the pin 962 ascending in the aperture 505 presses against the lamellae 605. By means of the oval shape of the cam 504 and the geometry of the aperture 961, the cam 504 has a deliberately greater vertical play in the aperture 961 than its horizontal play. The reduced surface pressure now affords easier mobility of the shutter 400 upon inhalation.
FIG. 20C In situation A5—the inhaler is closed again after an omitted inhalation—the valve shield 800 remained in its position, i.e. it was not sucked forwards. When the protective cap 950 is applied, the carriage 500 is pushed back; its spring tongues 513 move away from the catches 321 of the dosing slide 300. The valve shield 800 is again pushed into its rearmost position by the carriage 500; the shutter 400 is locked again. The dosing slide 300 remains, however, with its filled dosing cavity 302 in its forward position; it remains there as a result of suitable friction.
FIGS. 20D In situation A6—inhalation was interrupted when incomplete—the valve shield 800 has not yet reached its forward position, as a result of which the shutter 400 was not yet displaced, and the dose of medicament remained enclosed. When the protective cap 950 is applied and the carriage 500 pushed back, the dosing slide 300 remains with its unemptied dosing cavity 302 at the front. The spring tongues 513 of the carriage 500 strike via the spring wedges 514 against the catches 321 and are thus bent inwards. In this way the spring wedges 514 strike against the locking teeth 824 and thus push the valve shield 800 back, until the further pushing back of the valve shield 800 by the two struts 508 and 510 of the carriage 500 takes place.
FIG. 20E After incomplete inhalation and reclosing of the inhaler—situation A8—the filled dosing slide 300 stands forward, while the valve shield 800 and carriage 500 are again situated in the rear starting position.
FIG. 20F In situation A7—after completed inhalation—the protective cap 950 is swung fully down, as a result of which the pins 962 have lifted the lamellae 605 of the funnel holder 601 and the wings 405 of the shutter 400 have been unlocked. During a correct inhalation, the valve shield 800 has been sucked forwards. The spring arms 822 with the wedge profiles 823 have surmounted the overspring ribs 157 in the upper part 150 of the housing as a result of the valve shield 800 moving forwards. The shutter 400 was pushed into its front end position by the advancing valve shield 800, by which the means the dosing cavity 302 became free and the medicament was inhaled by the patient.

During a correct inhalation the valve shield 800 has been sucked forwards, after its spring arms 822 with the wedge profile 823 have surmounted the overspring ribs 157. It is possible to define the necessary suction effort with the geometry of the wedge profile 823 and of the overspring ribs 157, and with the elasticity of the spring arms 822. In the frontmost position of the valve shield 800, the two elastic spring arms 825 with the hooks 826 arranged thereon are driven behind the hooks 122 arranged in the lower part 100 of the housing. This prevents the valve shield 800 from automatically sliding back.

During the reverse movement of the carriage 500, its spring wedges 514 sit clamped between the catches 321 and the locking teeth 824 and cannot therefore escape. As a result, the dosing slide 300 and the valve shield 800 are now pushed back into the starting position—Situation A1—by the spring wedges 514 and the struts 508, 510. In so doing, the hooks 826, 122 are released from one another.

FIGS. 21A to 21C

This sequence of figures illustrates the function of the blocking hooks 140 employed in the interaction with the mouthpiece 900 and the side arms 960 of the protective cap 950.

FIG. 21A

In the starting position B1, the protective cap 950 is closed, i.e. pushed on; the mouthpiece 900 however is absent when fitting the blocking hooks 140. The spring arms 142 protrude through the apertures 117 in the bars 106, support themselves therein and force the levers 143 outwards. The blocking teeth 144 strike the solid side arms 960 of the protective cap 950.

FIG. 21B

Here—in the incorrect position B2—the protective cap 950 is pulled out and swung down; the carriage 500 is pulled forward, so that the spring arms 142 are pressed back into the apertures 117 by the carriage 500, as a result of which the levers 143 are under increased tensioning. The mouthpiece 900 has been removed, however, for example for a cleaning procedure. The blocking teeth 144 now engage in the apertures 970 present in the side arms 960, since the levers 143 are forced outwards by the pressure of the spring arms 142. In this state, the protective cap 950 cannot be swung up in order to push it in. Thus, the absence of the mouthpiece 900 is made evident, and this precludes a situation where the patient puts the inhaler away without the mouthpiece 900 being fitted and cannot then use the inhaler in an emergency.

FIG. 21C

In the desired position B3, the mouthpiece 900 is fitted. The connector plugs 911 of the mouthpiece 900 project into the receiving notches 109. The bevels 931 of the connector plugs 911 here press the catches 145 of the levers 143 inwards, counter to the tensioning of the spring arms 142, so that the blocking teeth 144 are drawn out of the apertures 970. The protective cap 950 can thus be swung up again and closed.

FIGS. 22A and 22B

With correct positioning of the inhaler, i.e. when there is no over-critical inclination in the horizontal or in the axial axis of rotation, the blocking balls 130 position themselves centrally in the ball sockets 108 at the deepest points. In such a position, the protective cap 950 can be pulled out, since the appended carriage 500 is not blocked and can also be moved out.

If the inclination is over-critical, then the blocking balls 130 roll from the deepest points onto the lateral limits 116,120 and now lie higher up because of the oblique slopes in the ball sockets 108. Outward travel of the carriage 500 is now blocked. The blocking balls 130 now come into collision with the impact ridges 524 and the bulges 516, so that ultimately the protective cap 950 cannot be pulled out. This safety measure guarantees that the inhaler is held in the correct position when it is opened, so that a correct filling of the dosing cavity 302 with medicament powder is ensured. The inhaler has to be opened in the prescribed position, but it can be used in any position once it has been opened, that is to say, in particular, also for patients who are lying down. A further control on its use is afforded by the fact that the protective cap 950 can only be swung downwards.

FIGS. 23A to 23G

This series of figures gives an impression of the successive construction of the inhaler, although this need not necessarily correspond with the sequence of assembly in mass manufacture.

The valve guide 850 is fitted into the rear of the lower part 100 of the housing and the valve shield 800 is fitted into the valve guide 850. The mouthpiece 900 projects from the front, only one half of the mouthpiece 900 being shown for reasons of improved clarity (FIG. 23A). The inhaler is equipped with the slide rail 200 placed near the mouthpiece 900 and with the carriage 500 bearing on the valve shield 800 (FIG. 23B). The dosing slide 300 is now placed on the slide rail 200 (FIG. 23C). The shutter 400 is added for further completion (FIG. 23D). The protective cap 950 with the lateral side arms 960, which are attached to the carriage 500, is now fitted (FIG. 23E). The completely fitted funnel arrangement 600, which is directed towards the protective cap 950, and the counter 700 are shown here in two views (23F, 23G). Finally, the upper part 150 of the housing would have to be fitted.

Further constructional variations can be made to the inhaler which has been described. The following variations are expressly mentioned here:

Instead of the dimples 972 for arresting the protective cap 950 in the pushed-in state—situation A1—an outwardly directed cam could in each case be provided near the entrance to the cap 952 on the upper side of the side arms 960 and engage in slots in the front side 160 of the upper part 150 of the housing in the closed state. In order to detach the protective cap 950 from the mouthpiece 900, the protective cap is to be pressed-in in the area of the lateral grip contours 951, as a result of which the cams come out.

In the mouthpiece 900, near the channel outlet 922, it is possible to provide in the enlarged channel section 928 a three-dimensional surface-profiled wall section with a transverse fluting in order to promote the powder deagglomeration and the deposition of coarser particles ineffective for inhalation.

To hold the two halves of the mouthpiece 900 together, complementary connecting elements could be arranged in each case on the inner cut edges of the two halves—for example, a combination of bores and cams—in order for both halves to be joined together again after possible cleaning and drying.

To embed the funnel arrangement in the inhaler, it might be possible to use a collar made of elastic material which is pushed onto the funnel holder 601.

The pharmacological dry powder stored in the funnel 690 can be in loose form on the one hand. However, pre-dosed units for dispensing are also included, for example as an extruded pellet lane or in pearl chain form. Individually dosed units for dispensing could be arranged in blisters or on tape rolls. It will be appreciated that the medicament reservoir and a device for dividing off the individual doses are to be designed in accordance with each other.

Irrespective of the greater outlay in terms of manufacturing technology, the above-described two-part housing, consisting of the lower part 100 of the housing and the upper part 150 of the housing, could also be made in one piece.

The atomizer path 924 in the mouthpiece 900 is designed as a straight or winding channel in which at least one baffle 925 is arranged, and the latter can be an inwardly projecting lamella, a wall, a flow body or a screen.

Instead of the mechanical counter 700, it is also possible to use a chip with which all relevant data are recorded, such as number of inhalations performed, time of intake, and flow parameters.

The flow control realized at present means of the over-spring rib 157 and the spring arms 822 could also be obtained by means of an alterable resistance within the valve guide 850.

To regulate the flow rate, it is advantageous to provide an insert for receiving an optional nozzle within the mouth tube 920, namely at the stat of the atomizer path 924 or mounted upstream of the mouth tube.

For specific changing of the flow resistance in the inhaler during an inhalation, which resistance is obtained by the air gap between the fixed valve guide 850 and the moving capsule 810 of the valve shield 800, it is possible to configure this air gap, effective at the respective position of the valve shield 800, incrementally by means of physical irregularities on the surface of the capsule 810 and/or in the inside of the valve guide 850. For this purpose, consideration may be given, for example, to widening or narrowing physical dimensions on the capsule 810 of the valve shield 800 and in the valve guide 850 or grooves whose cross-section changes along their length.

In the inhaler which has been described, but also in inhalers in general, there is the possibility of recording the inhalations and their flow parameters by means of sensor technology. To measure the parameters, use is made of membrane/bending beam technology or a piezoresistive element in combination with a diaphragm or in combination with the Venturi measurement principle. With IPC logic and sensor technology, open-loop control becomes closed-loop control. This closed-loop control makes it possible to govern an adjustable nozzle via an electronic movement element, which nozzle finally regulates the flow in the inhaler constantly by a resistance change.

For current supply, a dynamo is provided in the inside of the inhaler and generates an electric current when the protective cap 950 is opened or when air flows through the inhaler during the inhalation, this electric current being stored and being used to supply the electronic components.

The electronic components, as a plug-in, re-usable control module, can be removed from the inhaler so that a battery operation is possible. The inhalation data are collected by means of an integrated memory chip and made available to the doctor or pharmacist. Exact monitoring of the dose administration is thus possible.

The plug-in modules can be recharged on base units for further use and/or can be programmed so that only the contaminated part of the inhaler is to be discarded.

To better monitor the inhalation procedure, a mechanically and/or electronically generated acoustic and/or optical signal is emitted on completion of a successful or unsuccessful inhalation.

It is also possible to arrange the two complementary grate sections 515, 621 on the one hand on the carriage 500 and on the other hand on the lower part 100 of the housing or on the upper part 150 of the housing. So that vibrations occur only when the protective cap 950 is being pulled out—but not when it is being pushed back—one of the two grate sections 515, 621 can be taken out of operation on each replacement of the protective cap 950, e.g. on a component which is also movable.

The desiccant powder at present accommodated in the funnel lid 680 inside the chamber 681 could also be positioned inside the funnel holder 601.

The outer contours of the inhaler and the internal weight distribution mean that when it is laid on an essentially horizontal and dimensionally stable support, the inhaler always orients itself with the outlet 608 of the funnel holder 601 pointing downwards.

What is claimed is:

1. The inhaler for multiple dosed administration of a pharmacological dry power, comprising:

a housing including a lower part and an upper part;

a mouthpiece attached to an end of said housing, said mouthpiece including a channel extending therethrough;

a protective cap covering said mouthpiece, said protective cap being movable between a closed position and an open position;

a medicament reservoir located inside said housing, said medicament reservoir containing dry powder and including a funnel outlet;

a movable shutter positioned inside said housing, said shutter including a closure part which protrudes into said channel of said mouthpiece;

a movable dosing slide located inside said housing, said dosing slide movable between a receiving position and a dispensing position, said dosing slide including a dosing cavity positioned underneath said funnel outlet of said medicament reservoir when said dosing slide is in said receiving position, said dosing cavity being fillable with dry powder when said dosing slide is in said receiving position, said dosing slide moving into said dispensing position upon moving said protective cap from said closed position to said open position, said dosing cavity moving into said closure part and being surrounded by said closure part upon movement of said dosing slide into said dispensing position;

a movable valve shield positioned inside said housing, said valve shield being movable between a rest position and a forward position in response to suction generated during inhalation, said valve shield moving said shutter when said valve shield moves into said forward position, the movement of said shutter releasing said dosing cavity from said closure part to thereby permit the release of dry powder from said dosing cavity into said channel of said mouthpiece and to permit the inhalation of dry powder by a user of said inhaler;

locking means for locking said valve shield in said forward position only upon a defined minimum intensity of inhalation;

return means for returning said dosing slide to said receiving position only after a correctly completed inhalation, thereby returning said dosing cavity underneath said funnel outlet; and a recording unit positioned inside said housing, said recording unit recording the number of correctly performed inhalations and having a protrusion that moves from an initial position to a final position such that, when said protrusion reaches its final position, the protrusion obstructs the return means from moving said dosing slide into its receiving position, thereby preventing further use of the inhaler.

2. The inhaler according to claim 1, wherein said locking means includes at least one spring arm extending from said valve shield, each of said at least one spring arm having a wedge profile at an end thereof; and at least one rib positioned in said upper part of said housing, each of said at least one spring arm passing over a corresponding one of said at least one rib when the defined minimum intensity of inhalation is achieved.

3. The inhaler according to claim 1, wherein said return means includes a movable carriage positioned inside said housing, said carriage including two rearwardly projecting spring tongues, each spring tongue having a spring wedge located on an end thereof; and said dosing slide, including two downwardly directed catches located at an end of said dosing slide opposite said dosing cavity, each spring wedge pressing against a corresponding catch as said carriage is moved away from said mouthpiece, said dosing slide moving in conjunction with said carriage.

4. The inhaler according to claim 1, further comprising a longitudinally displaceable carriage positioned inside said housing, said carriage including two rearwardly projecting spring tongues, each spring tongue having a spring wedge located on an end thereof;

said dosing slide, including two downwardly directed catches located at an end of said dosing slide opposite said dosing cavity; and two side arms projecting from said protective cap, said side arms being connected to said carriage such that as said protective cap is moved from said closed position to said open position, said carriage is pulled toward said mouthpiece, each spring wedge pressing against a corresponding catch as said carriage is pulled toward said mouthpiece, such that said dosing slide is pulled toward said mouthpiece.

5. The inhaler according to claim 4, further comprising blocking means for blocking the movement of said protective cap when said inhaler is rotated about a central axis of said inhaler beyond a predetermined point.

6. The inhaler according to claim 5, wherein said blocking means includes at least one ball socket in said lower part of said housing;

a stepped bulge and two impact ridges positioned on an underside of said carriage, said bulge and said impact ridges corresponding to each of said at least one ball socket; and a movable blocking ball positioned in each of said at least one ball socket, and upon rotation of said inhaler about said central axis, said blocking ball blocks the movement of said carriage.

7. The inhaler according to claim 1, wherein said medicament reservoir includes a funnel holder;

a funnel positioned in said funnel holder;

a funnel lid positioned on said funnel; and a chamber located in said funnel lid, a hygroscopic desiccant powder contained in said chamber.

8. The inhaler according to claim 7, wherein hygroscopic desiccant powder is contained in a space provided in said funnel holder.

9. The inhaler according to claim 1, wherein the suction required to move the said shutter from its rest position to its forward position is determined by a resistance which said valve shield has to overcome during inhalation.

10. The inhaler according to claim 9, wherein said locking means creates said resistance and said locking means includes at least one spring arm extending from said valve shield, each of said at least one spring arm having a wedge profile at an end thereof; and at least one rib positioned in said upper part of said housing, each of said at least one spring arm passing over a corresponding one of said at least one rib when the defined minimum intensity of inhalation is achieved.

11. The inhaler according to claim 9, further comprising a valve guide surrounding said valve shield and an obstacle to be surmounted during movement of said valve shield inside said valve guide. whereby said resistance varies with the size and shape of said obstacle.

12. The inhaler according to claim 11, further comprising an air gap between said valve guide and said valve shield, said air gap being configured incrementally by physical irregularities in an inner surface of said valve guide and on an outer surface of said valve shield.

13. The inhaler according to claim 9, wherein said resistance is dependent upon the distance between said rest position and said forward position of said shutter, whereby said resistance varies in accordance with said distance.

14. The inhaler according to claim 1, wherein said mouthpiece includes a channel inlet;

a mouth tube having a channel outlet; and an atomizer path connecting said channel inlet and said channel outlet, said atomizer path including a first channel section having at least one baffle and a second channel section in communication with said first channel section, said second channel section having a larger volume than said first channel section, said second channel section having a wall section with a textured surface.

15. The inhaler according to claim 14, wherein said first channel section is straight.

16. The inhaler according to claim 14, wherein said first channel section has a winding configuration. screen.

17. The inhaler according to claim 14, wherein said mouth tube includes an end face having an upper region, said channel outlet being located in said upper region.

18. The inhaler according to claim wherein said mouthpiece is detachable from said housing.

19. The inhaler according to claim 18, said mouthpiece is connected to said housing by a plug connection.

20. The inhaler according to claim 14, wherein said mouthpiece is a multi-part component which can be opened after detachment from said housing.

21. The inhaler according to claim 20, wherein the parts of said mouthpiece are connected to one another by an integral hinge.

22. The inhaler according to claim 21, wherein said mouthpiece includes two symmetrical halves having corresponding complementary connecting elements, and wherein said integral hinge is located on an outer end face of said mouthpiece.

23. The inhaler according to claim 1, wherein said recording unit records additional relevant data on the use of said inhaler.

24. The inhaler according to claim 23, wherein said recording unit records the times and flow parameters of each use of said inhaler.

25. The inhaler according to claim 1, wherein said recording unit indicates the completion of an inhalation by generating a signal.

26. The inhaler according to claim 25, wherein said signal is acoustic.

27. The inhaler according to claim 25, wherein said signal is optical.

28. The inhaler according to claim 25, wherein said signal is acoustic and optical.

29. The inhaler according to claim 1, further comprising vibrating means for generating vibrations as said protective cap is moved from said closed position to said open position and while said dosing cavity is positioned underneath said funnel outlet of said medicament reservoir.

30. The inhaler according to claim 29, wherein said vibrating means includes a first grate section located on said lower part of said housing and a second grate section located on a movable carriage connected to said protective cap.

31. The inhaler according to claim 30, wherein said first grate section is located on said medicament reservoir.

32. The inhaler according to claim 1, further comprising
    first grip contours on said protective cap;
    preventing means for preventing said protective cap from being moved from said closed position to said open position, said preventing means being disengaged by pressing said protective cap in the area of said first grip contours;
    two side arms attached to said protective cap, said side arms being constructed such that moving said protective cap from said closed position to said open position requires said protective cap to be moved along a longitudinal axis of said inhaler before said protective cap is moved downward to said open position, thereby ensuring that the user places said inhaler in a proper operating position; and
    second grip contours on an exterior of said housing.

33. The inhaler according to claim 32, wherein said preventing means includes
    two safety cams located inside said housing, and
    a safety dimple located on each of said side arms near said protective cap, each safety dimple engaging a corresponding safety cam, thereby preventing movement of said protective cap.

34. The inhaler according to claim 32, wherein said second grip contours are grip dimples.

35. The inhaler according to claim 1, further comprising positioning means for positioning said protective cap in said open position.

36. The inhaler according to claim 35, wherein said positioning means includes
    two safety cams located inside said housing; and
    two side arms attached to said protective cap, each side arm including a locking dimple located opposite said protective cap, each locking dimple engaging a corresponding safety cam, thereby securing said protective cap in said open position.

37. The inhaler according to claim 1, further comprising prohibiting means for prohibiting said inhaler from being closed by moving said protective cap from said open position to said closed position when said mouthpiece has been removed from said inhaler.

38. The inhaler according to claim 37, wherein said prohibiting means includes at least one blocking hook positioned in said housing, each of said at least one blocking hook locking said protective cap in said open position when said mouthpiece is removed, each of said at least one blocking hook unlocking said protective cap from said open position upon insertion of said mouthpiece.

39. The inhaler according to claim 1, further comprising
    a valve guide having a bottom with a plurality of holes; and
    said valve shield, including a bottom with a plurality of stubs corresponding to said holes, said stubs engaging in said holes.

40. The inhaler according to claim 1, wherein
    said dosing cavity is an opening passing through said dosing slide; and
    a slide rail is positioned underneath said dosing slide, said slide rail extending along the length of said dosing cavity, thereby closing said dosing cavity from below when said dosing cavity is positioned underneath said funnel outlet of said medicament reservoir.

* * * * *